United States Patent [19]
Borrelli et al.

[11] Patent Number: 5,998,364
[45] Date of Patent: Dec. 7, 1999

[54] COMPONENT B AS CICATRIZANT

[75] Inventors: Francesco Borrelli; Silvia Donini; Fabrizio Martelli; Renato Mastrangeli, all of Rome, Italy

[73] Assignee: Applied Research Systems Ars Holding N.V., Curacao, Netherlands

[21] Appl. No.: 09/171,659

[22] PCT Filed: Apr. 24, 1996

[86] PCT No.: PCT/EP96/01702
§ 371 Date: Jan. 27, 1999
§ 102(e) Date: Jan. 27, 1999

[87] PCT Pub. No.: WO97/39765
PCT Pub. Date: Oct. 30, 1997

[51] Int. Cl.⁶ .................................................. A61K 38/00
[52] U.S. Cl. ................................................................ 514/2
[58] Field of Search ..................................... 514/2

[56] References Cited

FOREIGN PATENT DOCUMENTS

WO 94/14959  7/1994  WIPO .

*Primary Examiner*—Raymond Henley, III
*Attorney, Agent, or Firm*—Browdy and Neimark

[57] ABSTRACT

The present invention relates to the use of Component B as cicatrizant, in particular in the treatment of wounds, ulcers and other traumatic lesions to any of the tissues in the body.

1 Claim, 10 Drawing Sheets

COMPONENT B AS CICATRIZANT

This is a 371 of PCT/EP96/01702 filed Apr. 24, 1996.

The present invention relates to the use of Component B as cicatrizant, in particular in the treatment of wounds, ulcers and other traumatic lesions to any of the tissues in the body.

Component B is a 81-amino acid protein originally isolated from human urine. The human gene has been cloned and expressed in CHO cells as recombinant human Component B. The molecule has a molecular weight of about 8.9 kD. It has been thoroughly described in WO 94/14259.

Such protein contains ten cysteines and bears a motif typical of serine protease enzymes. Sequence alignment to a protein data bank has shown some homologies of Component B with known molecules such as CD59, urokinase receptor (uPA-R) and some venom toxins.

Data obtained by the Applicant from the study of organ and tissue distribution in mice showed that eye, lung and skin are the sites in which Component B RNA is mainly expressed. In human tissues, Component B was found to be highly expressed in the squamous epithelia and mucosae, such as skin, oesophagus and exocervix, as determined by immunohistochemistry. Finally, EGF has been found to induce the expression of Component B RNA in human squamous epidermoid A431 cells.

Component B has been reported to have antiinflammatory, anticoagulant and antitumoral activity, as well as an activity as inihibitor of the binding of TGF-α to its receptor.

The Applicant has now found that Component B is also useful as cicatrizant, and it is, therefore, in particular, useful in the treatment of wounds, ulcers and other traumatic lesions to any of the tissues in the body.

Therefore, the main object of the present invention is the use of Component B for the manufacture of a pharmaceutical composition useful as cicatrizant, in particular in the treatment of wounds, ulcers and other traumatic lesions to any of the tissues in the body.

A further object of this invention is a method of treatment of wounds, ulcers and other traumatic lesions to any of the tissues in the body, comprising administering an effective amount of Component B, together with a pharmaceutically acceptable excipient.

Another object of the invention are pharmaceutical compositions prepared as described above.

For the methods of preparation of Component B and for its amino acid sequence, reference is made to the disclosure of WO 94/14259.

The administration of the active ingredient may be by oral, intravenous, intramuscular, subcutaneous or topical route. Other routes of administration, which may establish the desired blood levels of the respective ingredients, are comprised by the present invention.

For the human therapy the preferred doses are 1 mg/kg or less for the systemic administration and 4 $\mu$g/cm$^2$ or less for the topical administration.

The invention will now be described by means of the following Examples, which should not be construed as in any way limiting the present invention. The Examples will refer to the Figures as specified here below.

EXAMPLES

Materials

Animals

Figure 1:
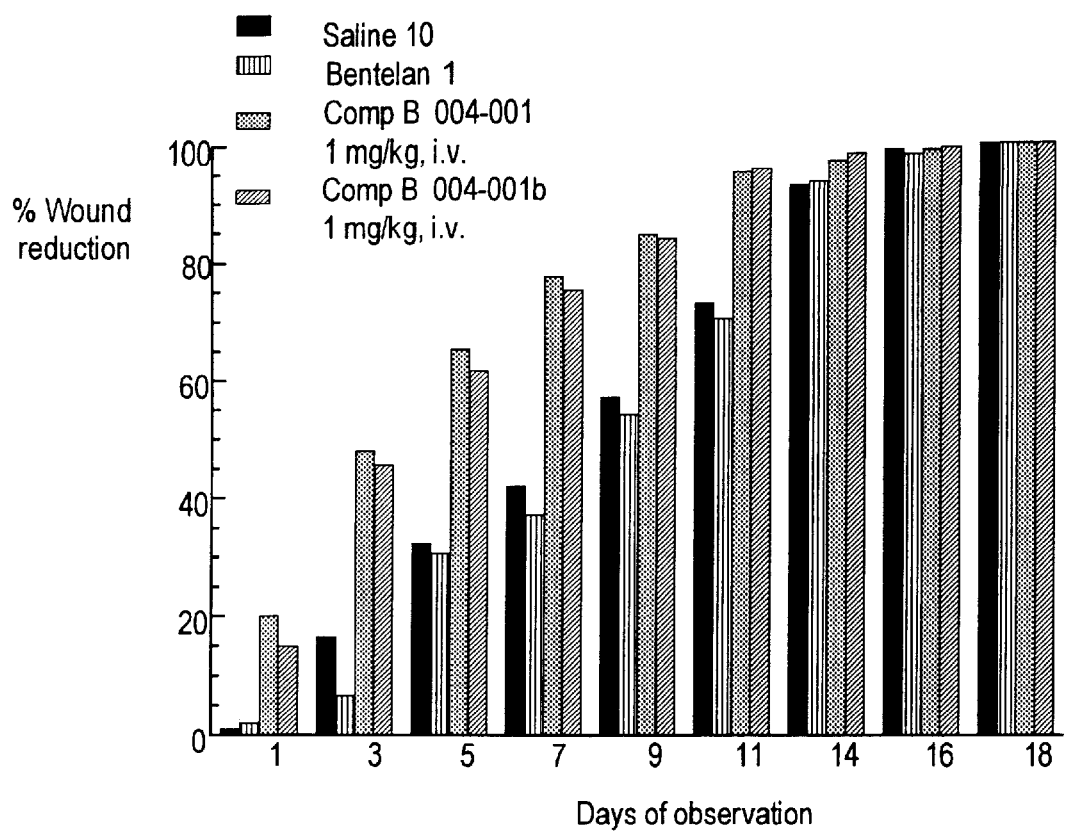
FIG. 1: the effect of the intravenous administration of Component B in comparison with that of betametasone (Bentelan®) on the experimental wound healing is shown. In particular, the results of Experiment 1 are summarised. Test drugs were administered daily for 6 consecutive days from day 0 (the day of wound induction) through 5.
Figure 2:
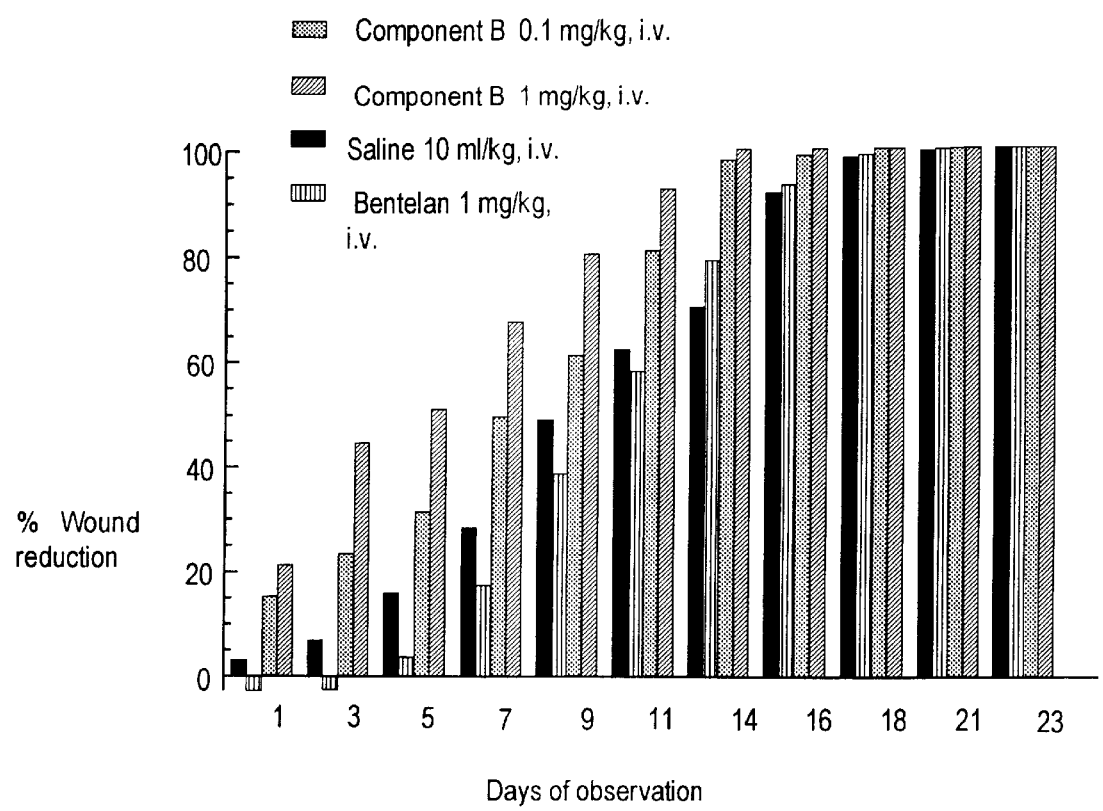
FIG. 2: the effect of the intravenous administration of Component B (batch 004-001b) in comparison with that of betametasone (Bentelan®) on the experimental wound healing is shown. In particular, the results of Experiment 2 are summarised. Test drugs were administered daily for 6 consecutive days from day 0 (the day of wound induction) through 5.
Figure 3:
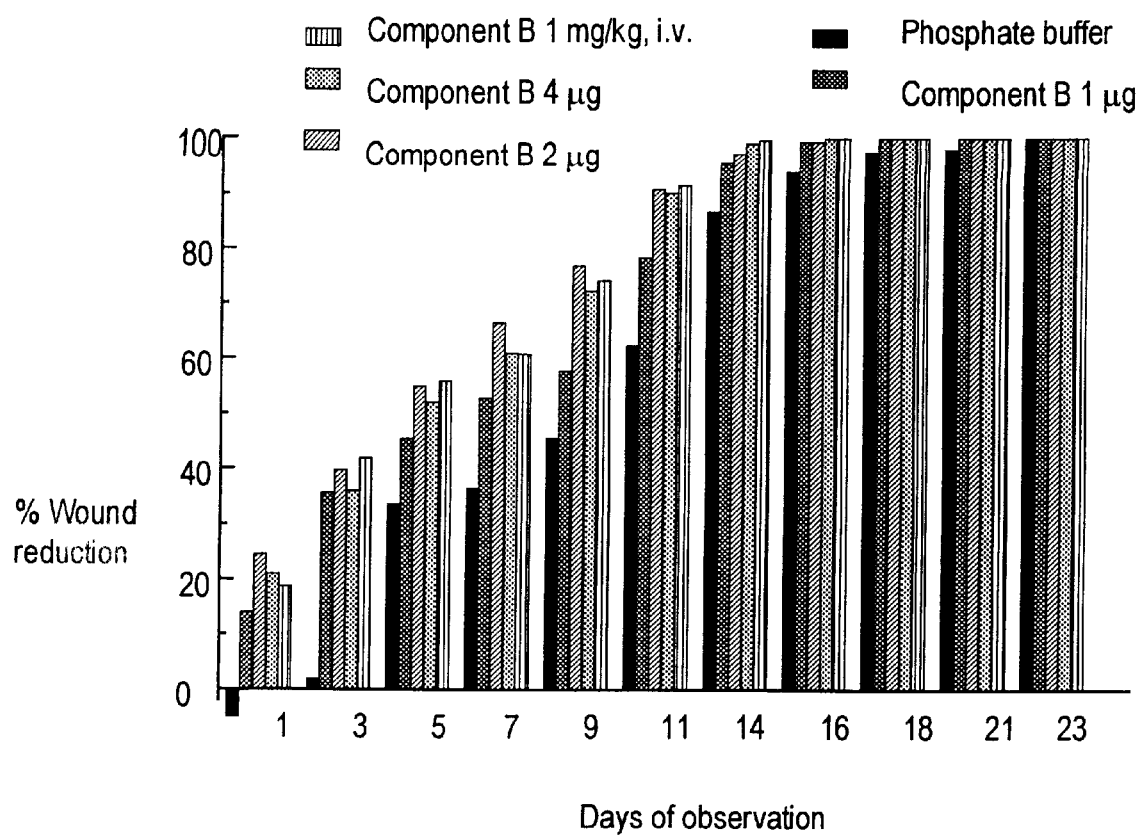
FIG. 3: the effect of the topical application of Component B (batch 004-001) on the experimental wound healing is shown. In particular, the results of Experiment 3 are summarised. Test drugs were topically applied for 5 consecutive days from day 0 (the day of wound induction) through 4.
Figure 4:
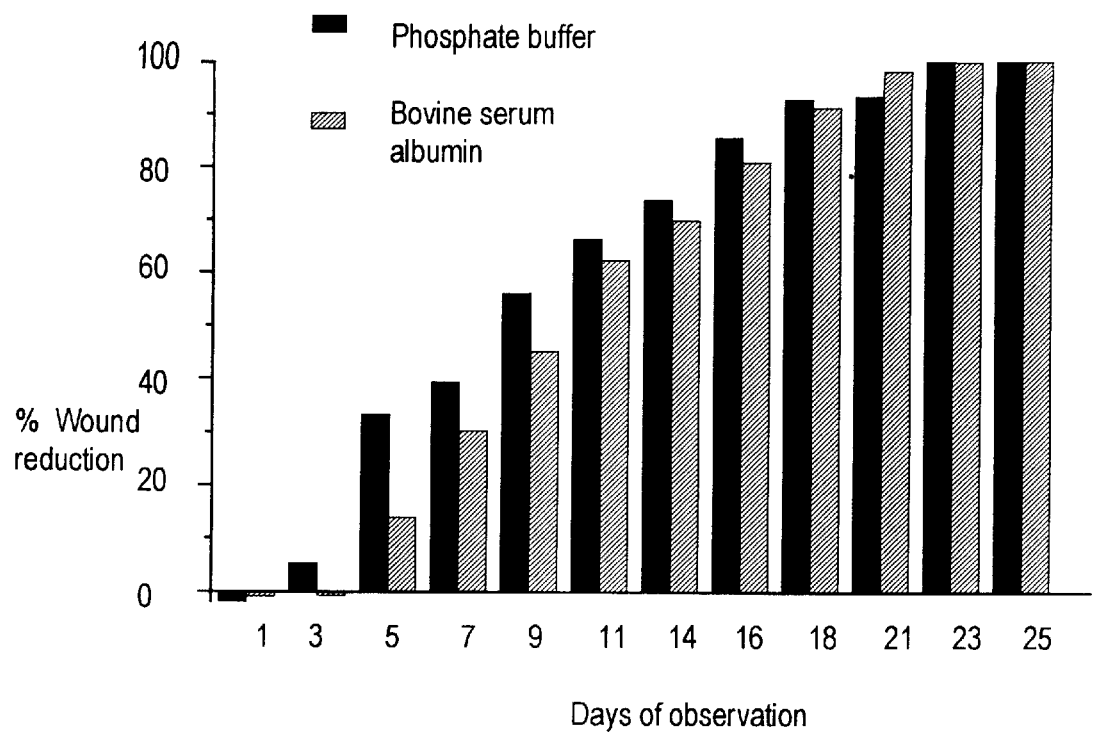
FIG. 4: the effect of the topical application of bovine serum albumin on the experimental wound healing is shown. In particular, the results of Experiment 4 are summarised. Test drugs were topically applied for 5 consecutive days from day 0 (the day of wound induction) through 4.

SPF CD-1 mice of both sexes, purchased from Charles River Italia (Calco, Como, Italy), were used for the experiments after an acclimatisation period of at least seven days under controlled environmental conditions (temperature 22±2° C.; humidity: 55±10% and a light/dark cycle of 12 hours).

Test compounds rec-hComponent B batch 004-001 (sulphated form) and 004-001b (non-sulphated form) expressed in CHO cells and produced essentially as described in WO 94/14259.

Commerical preparation of betametasone (Bentelan®) from Glaxo (Verona, Italy).

Sodium chloride 0.9% (saline), from Baxter (Trieste, Italy).

Bovine serum albumin (BSA), fraction V supplied by Sigma Chemical Co. (St. Louis Mo., USA).

Methods

Experimental full-thickness wound healing

The method used was that suggested by J. J. P. Morton and M. H. Malone (Morton J. J. P. and Malone M. H., Arch. Int. Pharmacodyn. 196: 117, 1972), who used this procedure for the evaluation of a number of drugs for their vulnerary activity in rats.

For the present study of Component B, the original method was suitably modified to be used in mice, as follows.

A circular ink mark (1 cm diameter) was impressed on the dorsal region of male mice (30–35 g, 6–7 week-old), and the skin of this marked area (including *panniculus carnosus* and adherent tissues) was excised using surgical scissors and forceps. The wound was then blotted dry with gauze pads until haemostasis occurred. On day 0, i. e. the day of surgery, longitudinal, transverse and two diagonal measurements (relative to the vertebral column) were made of the diameter of the wound to the nearest 0.1 mm using a direct reading caliper. The exact points of measurements were preserved by marking the adjacent skin with indelible ink. Subsequent wound measurements were made every other day except on Sunday up to complete wound closure. Both surgery and measurements were made under light ether anaesthesia of the mice.

The area of each wound was obtained by multiplying the square of its mean diameter by 0.7854. Per cent wound closure was then calculated relative to day 0. The mean per cent wound closure values for each measurement day were tabulated for each experimental group and the closure time 50% ($CT_{50}$) interpolated.

Systemic treatment

Two experiments (Experiments 1 and 2) were performed. In the second experiment, on each measurement day, the measurements were performed by the same operator who was unaware of the treatment schedules. In each experiment the animals were divided into 4 groups and treated according to the following schedule.

| Group number | 1st experiment | 2nd experiment |
|---|---|---|
| 1 | Saline 10 ml/kg, i.p. | Saline 10 ml/kg, i.v. |
| 2 | Component B 004-001, 1 mg/kg, i.v. | Component B 004-001b, 0.1 mg/kg, i.v. |
| 3 | Component B 004-001b, 1 mg/kg, i.v. | Component B 004-001b, 1 mg/kg, i.v. |
| 4 | Betametasone, 1 mg/kg, i.p. | Betametasone, 1 mg/kg, i.v. |

The animals were treated once a day for 6 consecutive days. The body weight of the animals was monitored for the whole duration of the study.

Topical treatment

In a further experiment (Experiment 3) the effect of the topical application of different doses of Component B (batch 004-001) were studied by using the already described procedure for wound induction following the treatment schedule reported in the table herebelow.

| Group number | Treatment |
|---|---|
| 1 | Phosphate buffer 0.05 ml, topically |
| 2 | Component B 004-001, 1 µg, topically |
| 3 | Component B 004-001, 2 µg, topically |
| 4 | Component B 004-001, 4 µg, topically |
| 5 | Component B 1 mg/kg, i.v. |

The solutions of the test product were applied (volume 0.05 ml) onto the wounds on days 1 and 2, whereas in the successive days, when the scab had been formed, they were injected underneath the scab by a syringe equipped with a 25 G needle.

Component B administered i.v. at the dose of 1 mg/kg, has been used as positive reference standard.

To rule out the possibility of aspecific effects of topical application of a proteic solution, in a parallel experiment the effect of BSA, at the same molar concentrations ($8.8\times10^{-6}$M) as Component B, was assayed topically in comparison to phosphate buffer (Experiment 4).

Results

Wound healing

FIG. 1 reports the data of the first Experiment, in which the activity of two batches (004-001 and 004-001b) of Component B were compared. Both of them were capable of accelerating the cicatrization process, their effects being already evident after 1 day of treatment. $CT_{50}$, i.e. the time when 50% wound reduction occurs, is 3.0 and 3.4 days, respectively, these values being not statistically different. By contrast, $CT_{50's}$ of 7.8 and 7.2 days were observed with betametasone (Bentelan®) and saline, respectively (see the paragraph entitled "Statistical Analysis").

In the second Experiment (FIG. 2) two doses of Component B (batch 004-001b) were studied. At the highest dose, 1 mg/kg, the $CT_{50}$ was 3.7 days whereas it was of 6.6 days at the lowest dose (0.1 mg/kg). The saline and betametasone treated groups displayed $CT_{50}$'s of 9.1 and 10 days, respectively (see the paragraph entitled "Statistical Analysis").

The positive effect of Component B on wound healing was also confirmed by another index, namely $ET_{50}$, indicating the time when 50% of the animals showed complete wound closure (see the paragraph entitled "Statistical Analysis").

The results of the experiment where Component B (batch 004-001) was applied topically onto the wound (Experiment 3), are reported in FIG. 3. The compound was studied at doses of 1, 2 and 4 μg/day for 5 consecutive days. All doses assayed were capable of enhancing the wound healing process as compared to controls. In particular, doses of 2 and 4 μg provided $CT_{50}$ values of 3.8 and 4.4, respectively, which are comparable to that found (3.9) with 1 mg/kg of Component B given i.v. With the lowest dose (1 μg), a $CT_{50}$ value of 5.3 days was observed, which is higher than those obtained with the other two topical doses, but still significantly different from controls (see the paragraph entitled "Statistical Analysis").

These data suggest that a dose of 2 μg, topically applied on the wound, produces the maximal effect and that 1 μg is still effective in enhancing the cicatrization process.

In order to verify whether the positive effect of Component B on the wound healing process is a specific characteristic of the product, a parallel experiment was carried out, in which the effect of BSA, at the same molar concentration of Component B, was compared to that of phosphate buffer (Experiment 4). These data are reported in FIG. 4. $CT_{50}$'s of 9.9 and 7.9 days were recorded with BSA and phosphate buffer, respectively. The above values are not significantly different (see the paragraph entitled "Statistical Analysis"), thus indicating that a standard protein solution, like BSA, does not influence the cutaneous wound repair.

The individual data of these experiments were reported in Tables 1A–4B.

Statistical Analysis

Statistical strategy

The statistical analysis was aimed at comparing the effect over the time of two preparations of Component B (Comp. B) both vs saline and the reference drug Bentelan.

Furthermore, the effects of the systemic and the topical administration of one preparation of Component B have been also evaluated.

In accordance with the treatment protocol the effect of the test drugs was studied considering the entire observation period.

The wound reduction experiment was repeated twice in order to confirm the Comp B effect at different dose levels.

Statistical test

The Sigmoidal Dose Response Analysis for the evaluation of the $CT_{50}$ (i.e. the time when the wound area is reduced by 50%) was used as the statistical test (see Finney D. J., Biometrics, 32, pp. 721–40, 1976).

Statistical units

1) Wound reduction ($CT_{50}$): Average percentage of variation vs average basal values.
2) Cumulative Frequency ($ET_{50}$): Cumulative frequency of animals showing a complete wound closure at each time point.

Groups of treatment (Exp. No 1)
1-Saline—10 ml/kg/day, i.p. for 6 days
2-Bentelan—1 mg/kg/day, i.p. for 6 days
3-CompB 004-001—1 mg/kg/day, i.v. for 6 days
4-CompB 004-001b—1 mg/kg/day, i.v. for 6 days
Groups of treatment (Exp. No 2)
1-Saline—10 ml/kg/day, i.v. for 6 days
2-Bentelan—1 mg/kg/day, i.v. for 6 days
3-CompB 004-001b—0.1 mg/kg/day, i.v. for 6 days
4-CompB 004-001b—1 mg/kg/day, i.v. for 6 days
Groups of treatment (Exp. No 3)
1-Phosphate buffer—50 µl/day, topical for 5 days
3-CompB 004-001—1 µg/day, topical for 5 days
3-CompB 004-001—2 µg/day, topical for 5 days
4-CompB 004-001—4 µg/day, topical for 5 days
5-CompB 004-001—1 mg/kg/day, i.v. for 5 days
Groups of treatment (Exp. No 4)
1-Phosphate buffer—50 µl/day, topical for 5 days
2-Bovine serum albumin (BSA)—50 µl/day ($8.8 \times 10^{-6}$ M), topical for 5 days
Treatment schedule (for Experiments 1, 2, 3 and 4)
Phase 1: Repeated treatment days according to the above treatment-group description.
Phase 2: Observation period up to the day of complete wound closure.

Results of the Statistical Analysis

The diagrams (sigmoidal dose response analysis) reported in FIGS. 5–10 summarise the effect of the test drugs as the variable the wound area.

Experiment 1

Figure 5:
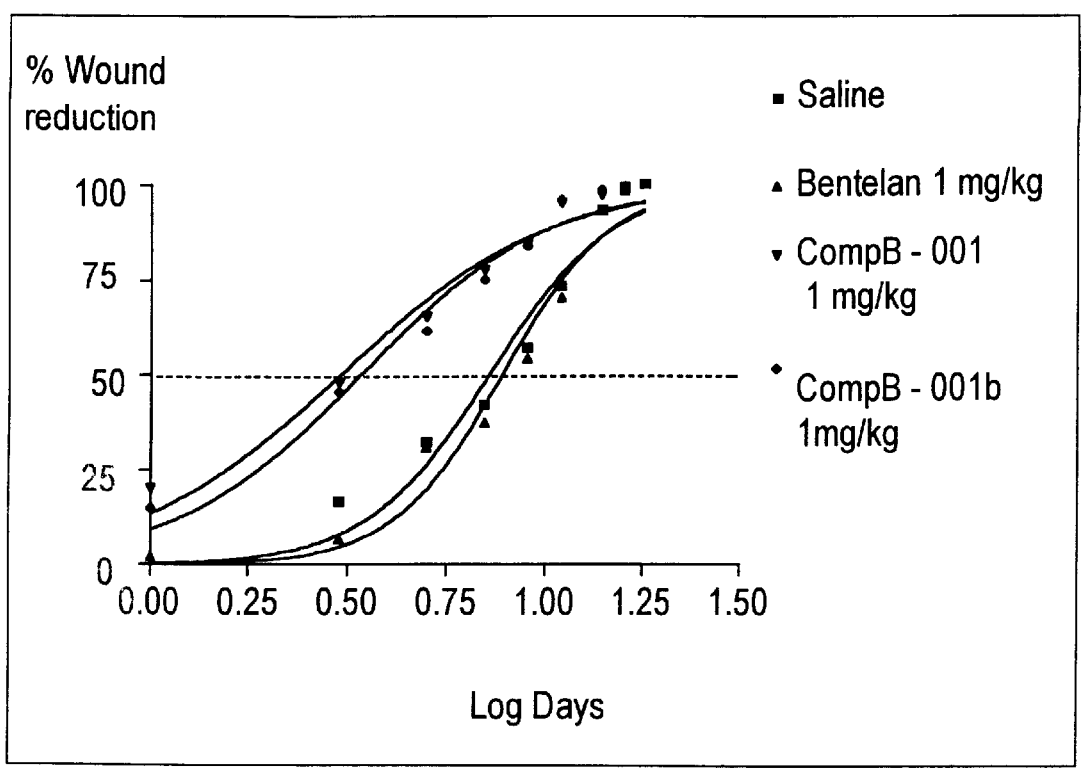
FIG. 5: the sigmoidal dose response analysis applied to the results of Experiment 1 is reported. The effect of the intravenous administration of Component B (batches 004-001 and 004-001b, indicated as "001" and "001b", respectively) and betametasone (Bentelan ®) on the experimental wound healing is, therefore, statistically evaluated on the basis of the results of Experiment 1.

Reference is made to FIG. 5.

The results of the sigmoidal dose response analysis ($CT_{50}$) applied to the wound area, relative to experiment 1, are reported in the following table.

| Test Drug | $CT_{50}$ (days) | Confidence Limits | $R^2$ |
|---|---|---|---|
| Saline | 7.2 | 6.2–8.3 | 0.96 |
| Bentelan 1 mg/kg | 7.8 | 6.9–8.8 | 0.97 |
| CompB 004-001 1 mg/kg | 3.0 | 2.5–3.7 | 0.97 |
| CompB 004-001b 1 mg/kg | 3.4 | 2.8–4.1 | 0.97 |

Experiment 2

Figure 6:
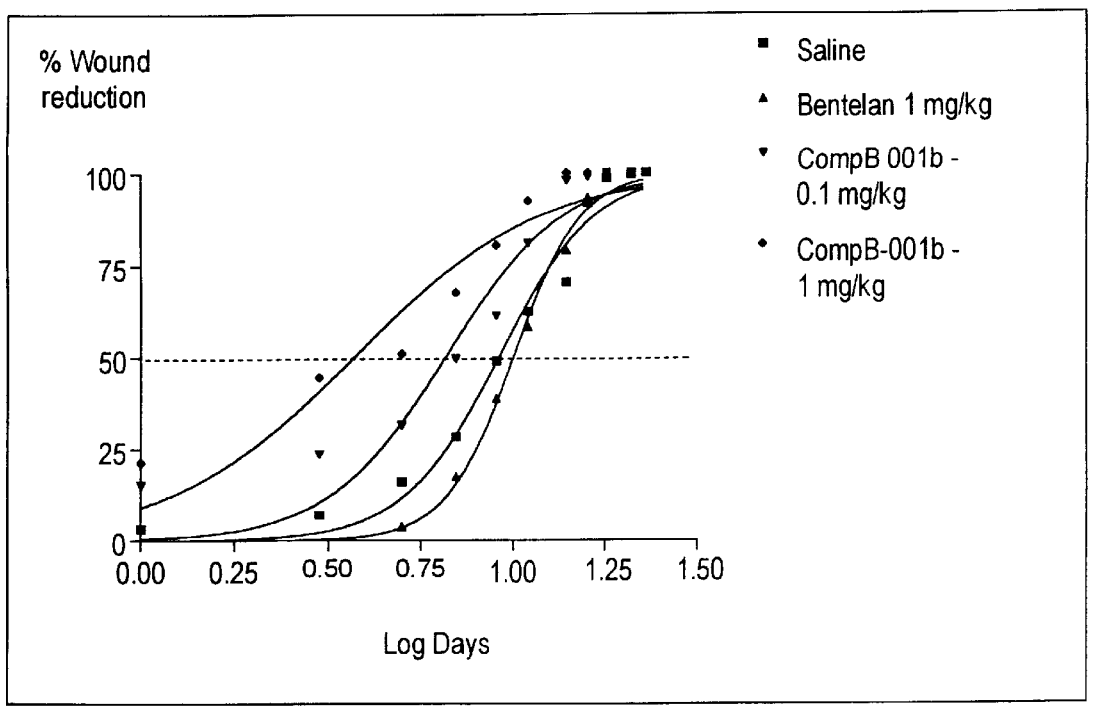
FIG. 6: the sigmoidal dose response analysis applied to the results of Experiment 2 is reported. The effect of the intravenous administration of Component B (batch 004-001b, indicated as "001b") and betametasone (Bentelan®) on the experimental wound healing is, therefore, statistically evaluated on the basis of the results of Experiment 2.

Reference is made to FIG. 6.

The results of the sigmoidal dose response analysis ($CT_{50}$) applied to the wound area, relative to experiment 2 are reported in the following table.

| Test Drug | $CT_{50}$ (days) | Confidence Limits | $R^2$ |
|---|---|---|---|
| Saline | 9.1 | 8.4–9.9 | 0.98 |
| Bentelan 1 mg/kg | 10.0 | 9.6–10.4 | 0.99 |
| CompB 004-001b 0.1 mg/kg | 6.6 | 5.5–7.7 | 0.94 |
| CompB 004-001b 1 mg/kg | 3.7 | 2.8–4.8 | 0.92 |

Combination of Experiments 1 and 2

Figure 7:
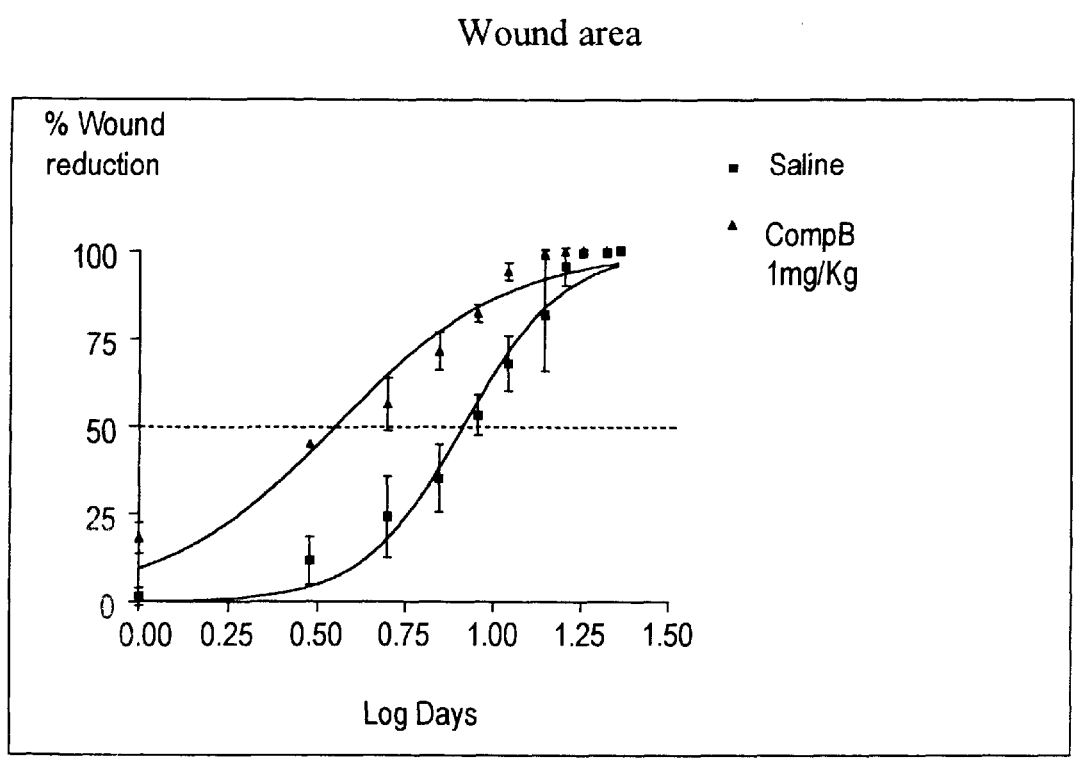
FIG. 7: the sigmoidal dose response analysis applied to the cumulated results of Experiments 1 and 2 is reported. The effect of the intravenous administration of Component B (batch 004-001b) on the experimental wound healing is, therefore, statistically evaluated on the basis of the combination of the results of Experiments 1 and 2.

Reference is made to FIG. 7.

The results obtained from the combination of the data of treatment groups common to both experiments 1 and 2, i.e. saline vs CompB-004-001b 1 mg/kg are summarised.

In addition, the frequency over the time of the animals showing complete closure of the wound was also evaluated (by Sigmoidal Dose-Response Analysis) from the cumulated data of Experiments 1 and 2.

The results of the sigmoidal dose response analysis ($CT_{50}$) applied to the wound area, relative to the combination of experiments 1 and 2, are reported in the following table.

| Test Drug | $CT_{50}$ (days) | Confidence Limits | $R^2$ |
|---|---|---|---|
| Saline | 8.2 | 7.5–8.9 | 0.95 |
| CompB 004-001b 1 mg/kg | 3.5 | 3.0–4.1 | 0.95 |

Figure 8:
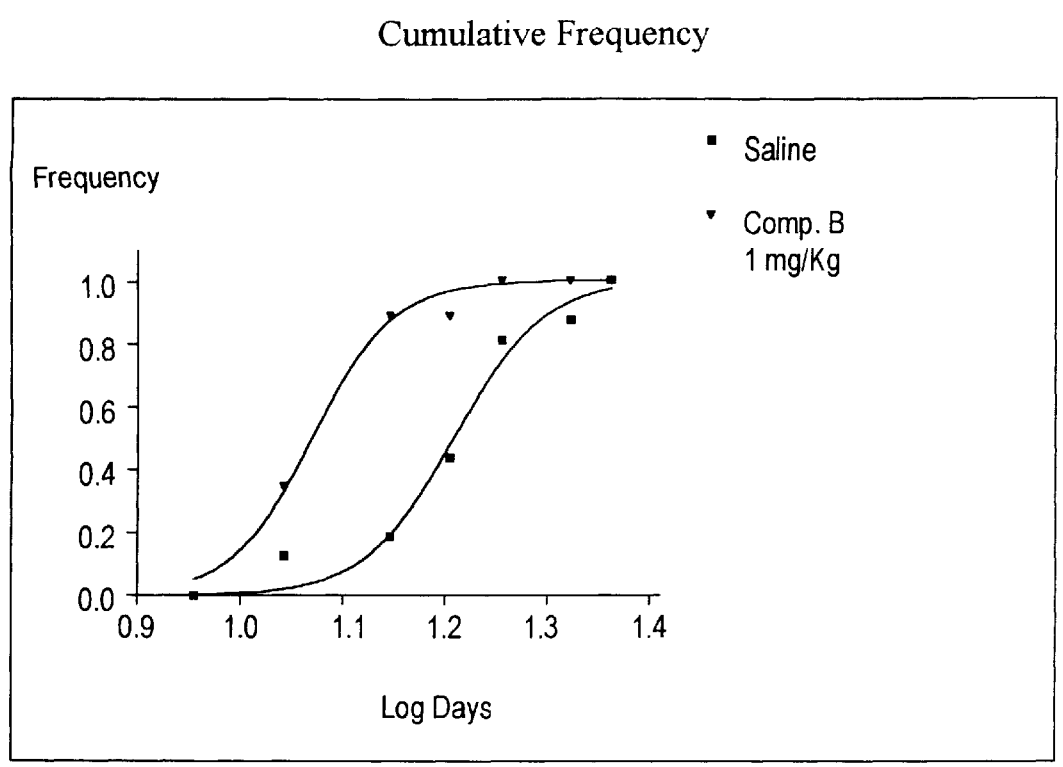
FIG. 8: the sigmoidal dose response analysis applied to the cumulative frequency, relative to combination of Experiments 1 and 2 is reported. The effect of Component B (batch 004-001b) is so evaluated.

For the cumulative frequency, reference is made to FIG. 8.

The results of the sigmoidal dose response analysis ($ET_{50}$) applied to the cumulative frequency, relative to the combination of experiments 1 and 2, are reported in the following table.

| Test Drug | $ET_{50}$ (days) | Confidence Limits | $R^2$ |
|---|---|---|---|
| Saline | 16.1 | 15.4–16.9 | 0.98 |
| CompB 004-001b 1 mg/kg | 11.7 | 11.2–12.1 | 0.99 |

In conclusion, the comparison among $CT_{50}$ values and among $ET_{50}$ values is a good estimate of the effect of each test drug on the experimental model.

Both CompB-001 (1 mg/kg, i.v.) and CompB-001b (dose levels 0.1 mg/kg and 1 mg/kg, i.v.) were found to be statistically different from saline and Bentelan in Experiments 1 and 2. The results of the combination of treatment groups common to Experiments 1 and 2 confirm the effect of the i.v. route of administration with CompB 1 mg/kg.

Experiment 3

Figure 9:
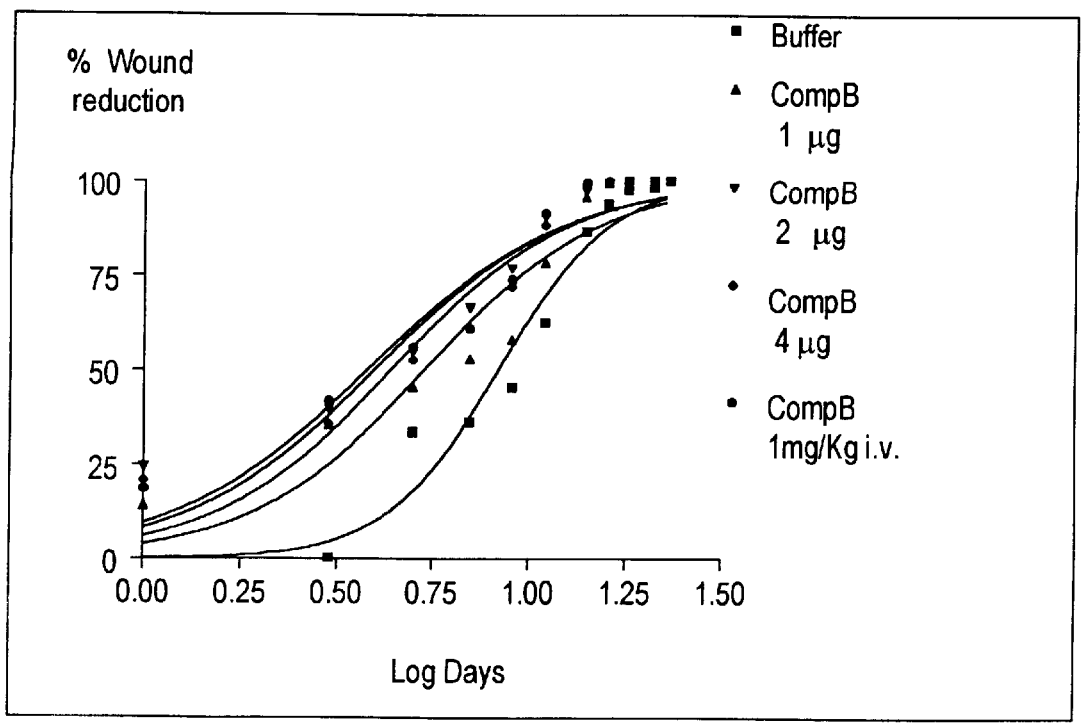
FIG. 9: the sigmoidal dose response analysis applied to the results of Experiment 3 is reported. The effect of the topical and intravenous administration of Component B (batch 004-001) on the experimental wound healing is, therefore, statistically evaluated on the basis of the results of Experiment 3.

Reference is made to FIG. 9.

A further set of experiments was performed in which the product was topically applied. The intravenous route was used as positive reference standard. The data were analysed using the same statistical models as above.

The results of the sigmoidal dose response analysis ($CT_{50}$) applied to the wound area, relative to experiment 3, are reported in the following table.

| Test Drug | $CT_{50}$ (days) | Confidence Limits | $R^2$ |
|---|---|---|---|
| Phosphate Buffer | 8.3 | 7.3–9.5 | 0.96 |
| CompB-001 1 mcg topical | 5.3 | 4.1–6.9 | 0.91 |
| CompB-001 2 mcg topical | 3.8 | 2.9–4.9 | 0.92 |
| CompB-001 4 mcg topical | 4.4 | 3.4–5.6 | 0.92 |
| CompB-001 1 mg/kg i.v. | 3.9 | 3.0–5.2 | 0.92 |

In conclusion, topical administration of CompB-001b showed, at all doses tested, a wound reduction ($CT_{50}$) significantly different from phosphate buffer.

Experiment 4

Figure 10:
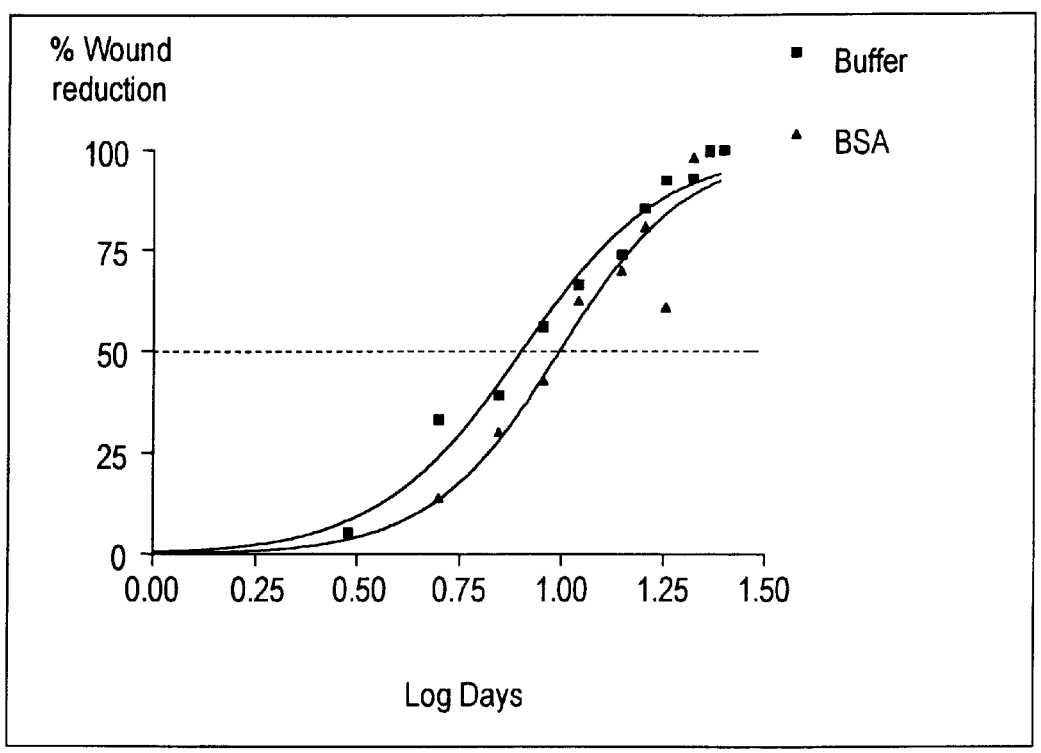
FIG. 10: the sigmoidal dose response analysis applied to the results of Experiment 4 is reported. A comparison of the effect between buffer and BSA in wound reduction is, therefore, statistically evaluated on the basis of the results of Experiment 4.

Reference is made to FIG. 10.

The diagram reports the comparison between topical application of phosphate buffer and BSA in wound reduction in order to rule out possible aspecific effects of Component B.

The results of the sigmoidal dose response analysis ($CT_{50}$) applied to the wound area, relative to Experiment 4, are reported in the following table.

| Test Drug | $CT_{50}$ (days) | Confidence Limits | $R^2$ |
|---|---|---|---|
| Buffer | 7.9 | 7.2–8.7 | 0.98 |
| BSA | 9.9 | 8.5–11.4 | 0.95 |

The above results did not show any differences between the topical application of phosphate buffer and BSA.

Conclusions of all the Study

The interesting result of this study is the activity of Component B in the cicatrization process both when administered intravenously or by topical application. The experimental model used in this study is directly related to the human trauma counterpart and is predictive for the application of Component B in the healing of traumatic lesions of the skin and in plastic and reconstructive surgery of mucosae and epithelia.

TABLE 1A

Wound healing data - Experiment 1
Comp B 004–001: 1 mg/kg, i.v.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.622 | 0.529 | −14.9518 | 0.318 | −48.8746 | 0.135 | −78.2958 | 0.06 | −90.3537 |
| 0.813 | 0.745 | −8.36408 | 0.566 | −30.3813 | 0.604 | −25.7073 | 0.483 | −40.5904 |
| 0.761 | 0.701 | −7.88436 | 0.341 | −55.1905 | 0.201 | −73.5874 | 0.111 | −85.4139 |
| 0.644 | 0.418 | −35.0932 | 0.289 | −55.1242 | 0.125 | −80.5901 | 0.103 | −84.0062 |
| 0.825 | 0.549 | −33.4545 | 0.266 | −67.7576 | 0.133 | −83.8788 | 0.049 | −94.0606 |
| 0.724 | 0.624 | −13.8122 | 0.432 | −40.3315 | 0.313 | −56.768 | 0.251 | −65.3315 |
| 0.679 | 0.697 | 2.650957 | 0.402 | −40.7953 | 0.214 | −68.4831 | 0.114 | −83.2106 |
| 0.769 | 0.478 | −37.8414 | 0.412 | −46.4239 | 0.3 | −60.9883 | 0.137 | −82.1847 |
| 0.709 | 0.48 | −32.299 | 0.374 | −47.2496 | 0.285 | −59.8025 | 0.195 | −72.4965 |
| | | | | Mean ± S.D. | | | | |
| 0.727 | 0.580 | −20.117 | 0.378 | −48.014 | 0.257 | −65.345 | 0.167 | −77.516 |
| 0.071 | 0.116 | 14.736 | 0.090 | 10.711 | 0.150 | 17.734 | 0.134 | 16.334 |

| Day 9 | | Day 11 | | Day 14 | | Day 16 | | Day 18 | |
|---|---|---|---|---|---|---|---|---|---|
| area | % variat. | area | % variat. | area | % variat. | area | % variat. | area | % variat. |
| 0.039 | −93.7299 | 0.031 | −95.0161 | 0 | −100 | 0 | −100 | 0 | −100 |
| 0.288 | −64.5756 | 0.104 | −87.2079 | 0.039 | −95.203 | 0.007 | −99.139 | 0 | −100 |
| 0.06 | −92.1156 | 0.009 | −98.8173 | 0 | −100 | 0 | −100 | 0 | −100 |
| 0.046 | −92.8571 | 0 | −100 | 0 | −100 | 0 | −100 | 0 | −100 |
| 0.043 | −94.7879 | 0 | −100 | 0 | −100 | 0 | −100 | 0 | −100 |
| 0.173 | −76.105 | 0 | −100 | 0 | −100 | 0 | −100 | 0 | −100 |
| 0.084 | −87.6289 | 0.104 | −84.6834 | 0.13 | −80.8542 | 0.046 | −93.2253 | 0 | −100 |
| 0.1 | −86.9961 | 0.06 | −92.1977 | 0 | −100 | 0 | −100 | 0 | −100 |
| 0.196 | −72.3554 | 0 | −100 | 0 | −100 | 0 | −100 | 0 | −100 |
| | | | | Mean ± S.D. | | | | | |
| 0.114 | −84.572 | 0.034 | −95.325 | 0.019 | −97.340 | 0.006 | −99.152 | 0 | −100.000 |
| 0.086 | 10.896 | 0.044 | 6.007 | 0.044 | 6.382 | 0.015 | 2.241 | 0.000 | 0.000 |

TABLE 1B

Wound healing data - Experiment 1
Comp B 004–001b: 1 mg/kg, i.v.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.535 | 0.505 | −5.60748 | 0.402 | −24.8598 | 0.273 | −48.972 | 0.162 | −69.7196 |
| 0.656 | 0.611 | −6.85976 | 0.194 | −70.4268 | 0.083 | −87.3476 | 0.017 | −97.4085 |

TABLE 1B-continued

Wound healing data - Experiment 1
Comp B 004–001b: 1 mg/kg, i.v.

| 0.647 | 0.631 | −2.47295 | 0.365 | −43.5858 | 0.3 | −53.6321 | 0.114 | −82.3802 |
|---|---|---|---|---|---|---|---|---|
| 0.813 | 0.508 | −37.5154 | 0.363 | −55.3506 | 0.177 | −78.2288 | 0.142 | −82.5338 |
| 0.781 | 0.622 | −20.3585 | 0.385 | −50.7042 | 0.289 | −62.9962 | 0.169 | −78.3611 |
| 0.785 | 0.656 | −16.4331 | 0.435 | −44.586 | 0.334 | −57.4522 | 0.205 | −73.8854 |
| 0.777 | 0.559 | −28.0566 | 0.397 | −48.906 | 0.361 | −53.5393 | 0.259 | −66.6667 |
| 0.724 | 0.618 | −14.6409 | 0.528 | −27.0718 | 0.455 | −37.1547 | 0.323 | −55.3867 |
| 0.747 | 0.756 | 1.204819 | 0.36 | −51.8072 | 0.244 | −67.336 | 0.256 | −65.7296 |
| 0.903 | 0.729 | −19.2691 | 0.561 | −37.8738 | 0.27 | −70.0997 | 0.175 | −80.6202 |
| | | | | Mean ± S.D. | | | | |
| 0.737 | 0.620 | −15.001 | 0.399 | −45.517 | 0.279 | −61.676 | 0.182 | −75.269 |
| 0.103 | 0.083 | 12.021 | 0.100 | 13.438 | 0.101 | 14.717 | 0.086 | 11.665 |

| Day 9 | | Day 11 | | Day 14 | | Day 16 | | Day 18 | |
|---|---|---|---|---|---|---|---|---|---|
| area | % variat. | area | % variat. | area | % variat. | area | % variat. | area | % variat. |
| 0.109 | 79.6262 | 0.075 | −85.9813 | 0.073 | −86.3551 | 0.028 | −94.7664 | 0 | −100 |
| 0 | −100 | 0 | −100 | 0 | −100 | 0 | −100 | 0 | −100 |
| 0.057 | −91.1901 | 0.054 | −91.6538 | 0 | −100 | 0 | −100 | 0 | −100 |
| 0.11 | −86.4699 | 0 | −100 | 0 | −100 | 0 | −100 | 0 | −100 |
| 0.069 | −91.1652 | 0.046 | −94.1101 | 0 | −100 | 0 | −100 | 0 | −100 |
| 0.146 | −81.4013 | 0.008 | −98.9809 | 0 | −100 | 0 | −100 | 0 | −100 |
| 0.179 | −76.9627 | 0.026 | −96.6538 | 0 | −100 | 0 | −100 | 0 | −100 |
| 0.235 | −67.5414 | 0.017 | −97.6519 | 0 | −100 | 0 | −100 | 0 | −100 |
| 0.196 | −73.7617 | 0 | −100 | 0 | −100 | 0 | −100 | 0 | −100 |
| 0.077 | −91.4729 | 0.049 | −94.5736 | 0 | −100 | 0 | −100 | 0 | −100 |
| | | | | Mean ± S.D. | | | | | |
| 0.118 | −83.959 | 0.028 | −95.961 | 0.007 | −98.636 | 0.003 | −99.477 | 0 | −100.000 |
| 0.072 | 9.844 | 0.027 | 4.533 | 0.023 | 4.315 | 0.009 | 1.655 | 0.000 | 0.000 |

TABLE 1C

Wound healing data - Experiment 1
Bentelan 1 mg/kg, i.p.

| Day 0 | Day 1 | | Day 3 | | Day 5 | | Day 7 | |
|---|---|---|---|---|---|---|---|---|
| area | area | % variat. | area | % variat | area | % variat. | area | % variat. |
| 0.671 | 0.634 | −5.51416 | 0.64 | −4.61997 | 0.507 | −24.4411 | 0.265 | −60.5067 |
| 0.76 | 0.737 | −3.02632 | 0.667 | −12.2368 | 0.535 | −29.6053 | 0.445 | −41.4474 |
| 0.703 | 0.737 | 4.836415 | 0.618 | −12.091 | 0.277 | −60.5974 | 0.246 | −65.0071 |
| 0.885 | 0.898 | 1.468927 | 0.697 | −21.2429 | 0.735 | −16.9492 | 0.759 | −14.2373 |
| 0.788 | 0.762 | −3.29949 | 0.799 | 1.395939 | 0.594 | −24.6193 | 0.626 | −20.5584 |
| 0.701 | 0.662 | −5.56348 | 0.705 | 0.570613 | 0.493 | −29.6719 | 0.46 | −34.3795 |
| 0.654 | 0.631 | −3.51682 | 0.666 | 1.834862 | 0.466 | −28.7462 | 0.491 | −24.9235 |
| | | | | Mean ± S.D. | | | | |
| 0.737 | 0.723 | −2.088 | 0.685 | −6.627 | 0.515 | −30.661 | 0.470 | −37.294 |
| 0.080 | 0.094 | 3.847 | 0.059 | 8.820 | 0.138 | 13.935 | 0.183 | 19.567 |

| Day 9 | | Day 11 | | Day 14 | | Day 16 | | Day 18 | |
|---|---|---|---|---|---|---|---|---|---|
| area | % variat. | area | % variat. | area | % variat. | area | % variat. | area | % variat. |
| 0.201 | −70.0447 | 0.199 | −70.3428 | 0.056 | −91.6542 | 0.011 | −98.3607 | 0 | −100 |
| 0.352 | −53.6842 | 0.339 | −55.3947 | 0.091 | −88.0263 | 0.008 | 98.9474 | 0 | −100 |
| 0.215 | −69.4168 | 0.084 | −88.0512 | 0 | −100 | 0 | −100 | 0 | −100 |
| 0.551 | −37.7401 | 0.331 | −62.5989 | 0.176 | −80.113 | 0.031 | −96.4972 | 0 | −100 |
| 0.535 | −32.1066 | 0.275 | −65.1015 | 0 | −100 | 0 | −100 | 0 | −100 |
| 0.302 | −56.9187 | 0.162 | −76.8902 | 0 | −100 | 0 | −100 | 0 | −100 |
| 0.263 | −59.7859 | 0.173 | −73.5474 | 0.031 | −95.2599 | 0.031 | −95.2599 | 0 | −100 |
| | | | | Mean ± S.D. | | | | | |
| 0.346 | −54.242 | 0.223 | −70.275 | 0.051 | −93.579 | 0.012 | −98.438 | 0.000 | −100.000 |
| 0.144 | 14.609 | 0.095 | 10.627 | 0.065 | 7.554 | 0.014 | 1.891 | 0.000 | 0.000 |

TABLE 1D

Wound healing data - Experiment 1
Saline 10 ml/kg, i.p.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.937 | 0.929 | −0.854 | 0.636 | −32.1238 | 0.398 | −57.524 | 0.275 | −70.651 |
| 0.997 | 0.948 | −4.915 | 0.675 | −32.2969 | 0.601 | −39.7192 | 0.463 | −53.5607 |
| 0.833 | 0.856 | 2.761 | 0.854 | 2.521008 | 0.793 | −4.80192 | 0.749 | −10.084 |
| 0.804 | 0.796 | −0.995 | 0.797 | −0.87065 | 0.767 | −4.60199 | 0.751 | −6.59204 |
| 0.697 | 0.825 | 18.364 | 0.605 | −13.1994 | 0.644 | −7.60402 | 0.64 | −8.17791 |
| 0.729 | 0.745 | 2.195 | 0.626 | −14.1289 | 0.454 | −37.7229 | 0.385 | −47.1879 |
| 0.618 | 0.645 | 4.369 | 0.518 | −16.1812 | 0.327 | −47.0874 | 0.209 | −66.1812 |
| 0.72 | 0.594 | −17.500 | 0.528 | −26.6667 | 0.287 | −60.1389 | 0.189 | −73.75 |
| | | | | Mean ± S.D. | | | | |
| 0.792 | 0.792 | 0.428 | 0.655 | −16.618 | 0.534 | −32.400 | 0.458 | −42.023 |
| 0.127 | 0.126 | 9.996 | 0.119 | 13.199 | 0.195 | 23.444 | 0.232 | 29.254 |

| Day 9 | | Day 11 | | Day 14 | | Day 16 | | Day 18 | |
|---|---|---|---|---|---|---|---|---|---|
| area | % variat. | area | % variat. | area | % variat. | area | % variat. | area | % variat. |
| 0.127 | −86.4461 | 0.139 | −85.1654 | 0 | −100 | 0 | −100 | 0 | −100 |
| 0.366 | −63.2899 | 0.297 | −70.2106 | 0.039 | −96.0883 | 0 | −100 | 0 | −100 |
| 0.608 | −27.0108 | 0.339 | −59.3037 | 0.151 | −81.8727 | 0.02 | −97.599 | 0 | −100 |
| 0.541 | −32.7114 | 0.36 | −55.2239 | 0.1 | −87.5622 | 0 | −100 | 0 | −100 |
| 0.512 | −26.5423 | 0.347 | −50.2152 | 0.128 | −81.6356 | 0.026 | −96.2697 | 0 | −100 |
| 0.331 | −54.5953 | 0.238 | −67.3525 | 0.012 | −98.3539 | 0 | −100 | 0 | −100 |
| 0.132 | −78.6408 | 0 | −100 | 0 | −100 | 0 | −100 | 0 | −100 |
| 0.085 | −88.1944 | 0 | −100 | 0 | −100 | 0 | −100 | 0 | −100 |
| | | | | Mean ± S.D. | | | | | |
| 0.338 | −57.179 | 0.215 | −73.434 | 0.054 | −93.189 | 0.006 | −99.234 | 0.000 | −100.000 |
| 0.206 | 26.106 | 0.151 | 19.519 | 0.063 | 8.172 | 0.011 | 1.463 | 0.000 | 0.000 |

TABLE 2A

Wound healing data - Experiment 2
Comp B 004–001b: 0.1 mg/kg, i.v.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.679 | 0.58 | −14.5803 | 0.561 | −17.3785 | 0.566 | −16.6421 | 0.347 | −48.8954 |
| 0.693 | 0.677 | −2.3088 | 0.635 | −8.36941 | 0.603 | −12.987 | 0.493 | −28.86 |
| 1.002 | 0.759 | −24.2515 | 0.84 | −16.1677 | 0.749 | −25.2495 | 0.525 | −47.6048 |
| 0.833 | 0.677 | −18.7275 | 0.701 | −15.8463 | 0.584 | −29.892 | 0.401 | −51.8607 |
| 0.671 | 0.597 | −11.0283 | 0.458 | −31.7437 | 0.412 | −38.5991 | 0.282 | −57.9732 |
| 0.651 | 0.526 | −19.2012 | 0.604 | −7.21966 | 0.556 | −14.5929 | 0.424 | −34.8694 |
| 0.682 | 0.755 | 10.70381 | 0.452 | −33.7243 | 0.512 | −24.9267 | 0.242 | −64.5161 |
| 0.817 | 0.601 | −26.4382 | 0.55 | −32.6805 | 0.486 | −40.5141 | 0.408 | −50.0612 |
| 0.693 | 0.538 | −22.3665 | 0.418 | −39.6825 | 0.307 | −55.6999 | 0.246 | −64.5022 |
| 0.799 | 0.58 | −27.4093 | 0.58 | −27.4093 | 0.461 | −42.3029 | 0.418 | −47.6846 |
| 0.777 | 0.686 | −11.7117 | 0.563 | −27.5418 | 0.433 | −44.2728 | 0.282 | −63.7066 |
| | | | | Mean ± S.D. | | | | |
| 0.754 | 0.634 | −15.211 | 0.578 | −23.433 | 0.515 | −31.425 | 0.379 | −49.683 |
| 0.105 | 0.081 | 11.420 | 0.120 | 10.927 | 0.117 | 13.897 | 0.098 | 11.427 |

| Day 9 | | Day 11 | | Day 14 | | Day 16 | |
|---|---|---|---|---|---|---|---|
| area | % variat. | area | % variat. | area | % variat. | area | % variat. |
| 0.347 | −48.8954 | 0.196 | −71.134 | 0.009 | −98.6745 | 0 | −100 |
| 0.309 | −55.4113 | 0.139 | −79.9423 | 0.039 | −94.3723 | 0.012 | −98.27 |
| 0.454 | −54.6906 | 0.146 | −85.4291 | 0.058 | −94.2116 | 0.018 | −98.20 |
| 0.206 | −75.2701 | 0.053 | −93.6375 | 0 | −100 | 0 | −100 |
| 0.238 | −64.5306 | 0.142 | −78.8376 | 0.04 | −94.0387 | 0 | −100 |
| 0.329 | −49.4624 | 0.216 | −66.8203 | 0.15 | −76.9585 | 0.052 | −92.01 |
| 0.179 | −73.7537 | 0.046 | −93.2551 | 0 | −100 | 0 | −100 |
| 0.282 | −65.4835 | 0.177 | −78.3354 | 0 | −100 | 0 | −100 |
| 0.231 | −66.6667 | 0.122 | −82.3954 | 0 | −100 | 0 | −100 |
| 0.409 | −48.811 | 0.203 | −74.5932 | 0 | −100 | 0 | −100 |

TABLE 2A-continued

Wound healing data - Experiment 2
Comp B 004–001b: 0.1 mg/kg, i.v.

| 0.225 | −71.0425 | 0.105 | −86.4865 | 0.008 | −98.9704 | 0 | −100 |
|---|---|---|---|---|---|---|---|
| | | | Mean ± S.D. | | | | |
| 0.292 | −61.274 | 0.140 | −80.988 | 0.027636 | −96.111 | 0.007 | −98.953 |
| 0.087 | 10.150 | 0.057 | 8.449 | 0.046 | 6.842 | 0.016 | 2.408 |

| Day 18 | | Day 21 | | Day 23 | |
|---|---|---|---|---|---|
| area | % variat. | area | % variat. | area | % variat. |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| | | | Mean ± S.D. | | |
| 0.000 | −100.000 | 0 | −100.000 | 0 | −100.000 |
| 0.000 | 0.000 | 0.000 | 0.000 | 0.000 | 0.000 |

TABLE 2B

Wound healing data - Experiment 2
Comp B 004–001b: 1 mg/kg, i.v.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.769 | 0.601 | −21.8466 | 0.455 | −40.8322 | 0.297 | −61.3784 | 0.121 | −84.2653 |
| 0.763 | 0.525 | −31.1927 | 0.493 | −35.3866 | 0.464 | −39.1874 | 0.451 | −40.8912 |
| 0.964 | 0.712 | −26.1411 | 0.358 | −62.8631 | 0.287 | −70.2282 | 0.134 | −86.0996 |
| 0.712 | 0.573 | −19.5225 | 0.421 | −40.8708 | 0.563 | −20.927 | 0.179 | −74.8596 |
| 0.763 | 0.59 | −22.6737 | 0.266 | −65.1376 | 0.155 | −79.6855 | 0.054 | −92.9227 |
| 0.793 | 0.747 | −5.80076 | 0.415 | −47.6671 | 0.334 | −57.8815 | 0.185 | −76.6709 |
| 0.785 | 0.451 | −42.5478 | 0.238 | −69.6815 | 0.199 | −74.6497 | 0.168 | −78.5987 |
| 0.747 | 0.701 | −6.15797 | 0.458 | −38.6881 | 0.398 | −46.7202 | 0.29 | −61.178 |
| 0.873 | 0.765 | −12.3711 | 0.73 | −16.3803 | 0.667 | −23.5968 | 0.515 | −41.008 |
| 0.979 | 0.867 | −11.4402 | 0.667 | −31.8693 | 0.594 | −39.3258 | 0.448 | −54.239 |
| 0.833 | 0.716 | −14.0456 | 0.594 | −28.6915 | 0.528 | −36.6146 | 0.395 | −52.581 |
| 1.225 | 0.72 | −41.2245 | 0.528 | −56.898 | 0.458 | −62.6122 | 0.384 | −68.6531 |
| | | | Mean ± S.D. | | | | | |
| 0.8505 | 0.664 | −21.247 | 0.469 | −44.581 | 0.412 | −51.067 | 0.277 | −67.664 |
| 0.145 | 0.117 | 12.337 | 0.148 | 16.249 | 0.161 | 19.536 | 0.156 | 17.540 |

| Day 9 | | Day 11 | | Day 14 | | Day 16 | |
|---|---|---|---|---|---|---|---|
| area | % variat. | area | % variat. | area | % variat. | area | % variat. |
| 0.056 | −92.7178 | 0.044 | −94.2783 | 0 | −100 | 0 | −100 |
| 0.344 | −54.9148 | 0.146 | −80.865 | 0 | −100 | 0 | −100 |
| 0.03 | −96.888 | 0 | −100 | 0 | −100 | 0 | −100 |
| 0.171 | −75.9831 | 0.021 | −97.0506 | 0 | −100 | 0 | −100 |
| 0.038 | −95.0197 | 0 | −100 | 0 | −100 | 0 | −100 |
| 0.061 | −92.3077 | 0.024 | −96.9735 | 0 | −100 | 0 | −100 |
| 0.039 | −95.0318 | 0 | −100 | 0 | −100 | 0 | −100 |
| 0.138 | −81.5261 | 0.038 | −94.913 | 0 | −100 | 0 | −100 |
| 0.344 | −60.5956 | 0.192 | −78.0069 | 0 | −100 | 0 | −100 |
| 0.186 | −81.001 | 0.019 | −98.0592 | 0 | −100 | 0 | −100 |
| 0.238 | −71.4286 | 0.159 | −80.9124 | 0 | −100 | 0 | −100 |
| 0.392 | −68 | 0.148 | −87.9184 | 0 | −100 | 0 | −100 |
| | | | Mean ± S.D. | | | | |
| 0.170 | −80.451 | 0.066 | −92.415 | 0 | −100.000 | 0 | −100.000 |
| 0.133 | 14.429 | 0.073 | 8.257 | 0.000 | 0.000 | 0.000 | 0.000 |

TABLE 2C

Wound healing data - Experiment 2
Bentelan 1 mg/kg, i.v.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.789 | 0.813 | 3.041825 | 0.767 | −2.78834 | 0.615 | −22.0532 | 0.565 | −28.3904 |
| 0.769 | 0.831 | 8.062419 | 0.846 | 10.013 | 0.833 | 8.322497 | 0.751 | −2.3407 |
| 0.805 | 0.741 | −7.95031 | 0.751 | −6.70807 | 0.763 | −5.21739 | 0.525 | −34.7826 |
| 0.751 | 0.86 | 14.51398 | 0.825 | 9.853529 | 0.997 | 32.75632 | 0.586 | −21.9707 |
| 0.842 | 0.864 | 2.612827 | 0.858 | 1.900238 | 0.773 | −8.19477 | 0.675 | −19.8337 |
| 0.856 | 0.739 | −13.6682 | 0.769 | −10.1636 | 0.712 | −16.8224 | 0.636 | −25.7009 |
| 0.651 | 0.679 | 4.301075 | 0.69 | 5.990783 | 0.626 | −3.84025 | 0.555 | −14.7465 |
| 0.769 | 0.679 | −11.7035 | 0.636 | −17.2952 | 0.656 | −14.6944 | 0.622 | −19.1157 |
| 0.763 | 0.86 | 12.71298 | 0.869 | 13.89253 | 0.777 | 1.834862 | 0.751 | −1.57274 |
| 0.675 | 0.679 | 0.592593 | 0.769 | 13.92593 | 0.709 | 5.037037 | 0.655 | −2.96296 |
| 0.805 | 0.667 | −17.1429 | 0.69 | −14.2857 | 0.72 | −10.559 | 0.622 | −22.7329 |
| 0.644 | 0.886 | 37.57764 | 0.809 | 25.62112 | 0.565 | −12.2671 | 0.551 | −14.441 |
| | | | | Mean ± S.D. | | | | |
| 0.760 | 0.775 | 2.746 | 0.773 | 2.496 | 0.729 | −3.808 | 0.625 | −17.383 |
| 0.070 | 0.086 | 14.999 | 0.073 | 13.020 | 0.115 | 14.627 | 0.074 | 10.667 |

| Day 9 | | Day 11 | | Day 14 | | Day 16 | |
|---|---|---|---|---|---|---|---|
| area | % variat. | area | % variat. | area | % variat. | area | % variat. |
| 0.317 | −59.8226 | 0.258 | −67.3004 | 0.151 | −80.8619 | 0.081 | −89.7338 |
| 0.424 | −44.8635 | 0.344 | −55.2666 | 0.222 | −71.1313 | 0.11 | −85.6957 |
| 0.457 | −43.2298 | 0.312 | −61.2422 | 0.181 | −77.5155 | 0.066 | −91.8012 |
| 0.755 | 0.532623 | 0.587 | −21.8375 | 0.369 | −50.8655 | 0.216 | −71.2383 |
| 0.545 | −35.2732 | 0.315 | −62.5891 | 0.117 | −86.1045 | 0.026 | −96.9121 |
| 0.43 | −49.7664 | 0.259 | −69.743 | 0.118 | −86.215 | 0.035 | −95.9112 |
| 0.396 | −39.1705 | 0.24 | −63.1336 | 0.071 | −89.0937 | 0 | −100 |
| 0.433 | −43.6931 | 0.309 | −59.8179 | 0.212 | −72.4317 | 0.025 | −96.749 |
| 0.594 | −22.1494 | 0.433 | −43.2503 | 0.092 | −87.9423 | 0.016 | −97.903 |
| 0.415 | −38.5185 | 0.325 | −51.8519 | 0.203 | −69.9259 | 0.036 | −94.6667 |
| 0.499 | −38.0124 | 0.302 | −62.4845 | 0.157 | −80.4969 | 0.013 | −98.3851 |
| 0.312 | −51.5528 | 0.124 | −80.7453 | 0.033 | −94.8758 | 0 | −100 |
| | | | Mean ± S.D. | | | | |
| 0.465 | −38.793 | 0.317 | −58.272 | 0.161 | −78.955 | 0.052 | −93.250 |
| 0.122 | 15.500 | 0.112 | 14.749 | 0.0881 | 11.768 | 0.061 | 8.146 |

| Day 18 | | Day 21 | | Day 23 | |
|---|---|---|---|---|---|
| area | % variat. | area | % variat. | area | % variat. |
| 0.02 | −97.4651 | 0 | −100 | 0 | −100 |
| 0.059 | −92.3277 | 0.047 | −99417 | 0 | −100 |
| 0.01 | −98.7578 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0.015 | −98.0494 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| | | Mean ± S.D. | | | |
| 0.009 | −98.883 | 0.004 | −99.951 | 0.000 | −100.000 |
| 0.017 | 2.250 | 0.014 | 0.168 | 0.000 | 0.000 |

TABLE 2D

Wound healing data - Experiment 2
Saline 10 ml/kg, i.v.

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.58 | 0.594 | 2.413793 | 0.535 | −7.75862 | 0.538 | −7.24138 | 0.466 | −19.6552 |
| 0.773 | 0.755 | −2.32859 | 0.763 | −1.29366 | 0.584 | −24.4502 | 0.561 | −27.4256 |
| 0.735 | 0.785 | 6.802721 | 0.779 | 5.986395 | 0.735 | 0 | 0.622 | −15.3741 |
| 0.805 | 0.666 | −17.2671 | 0.655 | −18.6335 | 0.615 | −23.6025 | 0.385 | −52.1739 |
| 0.701 | 0.629 | −10.271 | 0.629 | −10.271 | 0.546 | −22.1113 | 0.493 | −29.6719 |
| 0.686 | 0.671 | −2.18659 | 0.584 | −14.8688 | 0.535 | −22.0117 | 0.478 | −30.3207 |
| 0.601 | 0.59 | −1.83028 | 0.58 | −3.49418 | 0.536 | −10.8153 | 0.451 | −24.9584 |
| 0.759 | 0.747 | −1.58103 | 0.72 | −5.13834 | 0.627 | −17.3913 | 0.551 | −27.4045 |
| | | | | Mean ± S.D. | | | | |
| 0.705 | 0.680 | −3.281 | 0.656 | −6.934 | 0.590 | −15.953 | 0.501 | −28.373 |
| 0.080 | 0.075 | 7.423 | 0.090 | 7.796 | 0.069 | 8.978 | 0.074 | 10.892 |

| Day 9 | | Day 11 | | Day 14 | | Day 16 | |
|---|---|---|---|---|---|---|---|
| area | % variat. | area | % variat. | area | % variat. | area | % variat. |
| 0.325 | −43.9655 | 0.206 | −64.4828 | 0.206 | −64.4828 | 0.104 | −82.069 |
| 0.339 | −56.1449 | 0.238 | −69.2109 | 0.181 | −76.5847 | 0.116 | −84.9935 |
| 0.436 | −40.6803 | 0.187 | −74.5578 | 0.197 | −73.1973 | 0.067 | −90.8844 |
| 0.408 | −49.3168 | 0.28 | −65.2174 | 0.216 | −73.1677 | 0.047 | −94.1615 |
| 0.369 | −47.3609 | 0.249 | −64.4793 | 0.238 | −66.0485 | 0.036 | −94.8645 |
| 0.246 | −64.1399 | 0.273 | −60.2041 | 0.175 | −74.4898 | 0 | −100 |
| 0.282 | −53.0782 | 0.297 | −50.5824 | 0.201 | −66.5557 | 0.048 | −92.0133 |
| 0.469 | −38.2082 | 0.377 | −50.3294 | 0.24 | −68.3794 | 0.036 | −95.2569 |
| | | | Mean ± S.D. | | | | |
| 0.359 | −49.112 | 0.263 | −62.383 | 0.20675 | −70.363 | 0.057 | −91.780 |
| 0.076 | 8.541 | 0.059 | 8.460 | 0.024 | 4.524 | 0.038 | 5.807 |

| Day 18 | | Day 21 | | Day 23 | |
|---|---|---|---|---|---|
| area | % variat. | area | % variat. | area | % variat. |
| 0.027 | 95.3448 | 0 | −100 | 0 | −100 |
| 0.041 | −94.696 | 0.027 | −96.5071 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0.017 | −97.7602 | 0 | −100 | 0 | −100 |
| | | Mean ± S.D. | | | |
| 0.011 | −98.475 | 0.003 | −99.563 | 0.000 | −100.000 |
| 0.016 | 2.275 | 0.010 | 1.235 | 0.000 | 0.000 |

TABLE 3A

Wound healing data - Experiment 3
Component B (004–001) 1 μg

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.746 | 0.709 | −4.95979 | 0.584 | −21.7158 | 0.477 | −36.059 | 0.305 | −59.1153 |
| 0.92 | 0.659 | −28.3696 | 0.404 | −56.087 | 0.304 | −66.9565 | 0.242 | −73.6957 |
| 0.687 | 0.618 | −10.0437 | 0.466 | −32.1689 | 0.444 | −35.3712 | 0.41 | −40.3202 |
| 0.818 | 0.822 | 0.488998 | 0.503 | −38.5086 | 0.388 | −52.5672 | 0.372 | −54.5232 |
| 0.742 | 0.571 | −23.0458 | 0.451 | −39.2183 | 0.399 | −46.2264 | 0.372 | −49.8652 |
| 0.716 | 0.677 | −5.44693 | 0.636 | −I1.1732 | 0.548 | −23.4637 | 0.503 | −29.7486 |
| 0.833 | 0.638 | −23.4094 | 0.487 | −41.5366 | 0.402 | −51.7407 | 0.377 | −54.7419 |
| 0.659 | 0.52 | −21.0926 | 0.49 | −25.6449 | 0.425 | −35.5083 | 0.332 | −49.6206 |
| 0.738 | 0.724 | −1.89702 | 0.571 | −22.6287 | 0.491 | −33.4688 | 0.466 | −36.8564 |
| 0.705 | 0.545 | −22.695 | 0.233 | −66.9504 | 0.195 | −72.3404 | 0.152 | −78.4397 |

TABLE 3A-continued

Wound healing data - Experiment 3  
Component B (004–001) 1 μg

Mean ± S.D.

| | | | | | | | |
|---|---|---|---|---|---|---|---|
| 0.756 | 0.648 | −14.047 | 0.471 | −35.563 | 0.407 | −45.370 | 0.353 | −52.693 |
| 0.079 | 0.091 | 10.696 | 0.112 | 16.759 | 0.100 | 15.606 | 0.103 | 15.277 |

| Day 9 | | Day 11 | | Day 14 | | Day 16 | |
|---|---|---|---|---|---|---|---|
| area | % variat. | area | % variat. | area | % variat. | area | % variat. |
| 0.41 | −45.0402 | 0.129 | −82.7078 | 0.056 | −92.4933 | 0 | −100 |
| 0.181 | −80.3261 | 0.09 | −90.2174 | 0.008 | −99.1304 | 0 | −100 |
| 0.366 | −46.7249 | 0.15 | −78.1659 | 0.099 | −85.5895 | 0 | −100 |
| 0.345 | −57.824 | 0.198 | −75.7946 | 0.063 | −92.2983 | 0.033 | −95.9658 |
| 0.271 | −63.4771 | 0.12 | −83.8275 | 0 | −100 | 0 | −100 |
| 0.475 | −33.6592 | 0.267 | −62.7095 | 0.02 | −97.2067 | 0 | −100 |
| 0.35 | −57.9832 | 0.204 | −75.5102 | 0.045 | −94.5978 | 0 | −100 |
| 0.246 | −62.6707 | 0.11 | −83.308 | 0.017 | −97.4203 | 0 | −100 |
| 0.401 | −45.664 | 0.18 | −75.6098 | 0.031 | −95.7995 | 0.008 | −98.916 |
| 0.11 | −84.3972 | 0.189 | −73.1915 | 0.008 | −98.8652 | 0.008 | −98.8652 |

Mean ± S.D.

| | | | | | | | |
|---|---|---|---|---|---|---|---|
| 0.316 | −57.777 | 0.164 | −78.104 | 0.035 | −95.340 | 0.005 | −99.375 |
| 0.112 | 15.939 | 0.054 | 7.507 | 0.031 | 4.340 | 0.010 | 1.284 |

| Day 18 | | Day 21 | | Day 23 | |
|---|---|---|---|---|---|
| area | % variat. | area | % variat. | area | % variat. |
| 0 | 100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |

Mean ± S.D.

| | | | | | |
|---|---|---|---|---|---|
| 0 | −100.000 | 0 | −100 | 0 | −100 |
| 0.000 | 0.000 | 0.000 | 0.000 | 0.000 | 0.000 |

TABLE 3B

Wound healing data - Experiment 3  
Phosphate buffer

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.785 | 0.75 | −4.4586 | 0.747 | −4.84076 | 0.285 | −63.6943 | 0.271 | −65.4777 |
| 0.673 | 0.768 | 14.1159 | 0.731 | 8.618128 | 0.626 | −6.98366 | 0.612 | −9.06389 |
| 0.785 | 0.772 | 14.71025 | 0.747 | −4.84076 | 0.487 | −37.9618 | 0.439 | −44.0764 |
| 0.902 | 0.902 | 0 | 0.862 | −4.43459 | 0.754 | −16.408 | 0.739 | −18.071 |
| 0.785 | 0.742 | −5.47771 | 0.766 | −2.42038 | 0.535 | −31.8471 | 0.531 | −32.3567 |
| 0.694 | 0.694 | 0 | 0.672 | −3.17003 | 0.448 | −35.4467 | 0.433 | −37.6081 |
| 0.733 | 0.846 | 15.4161 | 0.743 | 1.364256 | 0.506 | −30.9686 | 0.487 | −33.5607 |
| 0.666 | 0.742 | 11.41141 | 0.778 | 16.81682 | 0.535 | −19.6697 | 0.475 | −28.6787 |
| 0.768 | 0.765 | −0.39063 | 0.687 | −10.5469 | 0.312 | −59.375 | 0.322 | −58.0729 |

Mean ± S.D.

| | | | | | | | | |
|---|---|---|---|---|---|---|---|---|
| 0.755 | 0.776 | 5.036 | 0.748 | −0.384 | 0.499 | −33.595 | 0.479 | −36.330 |
| 0.074 | 0.062 | 8.698 | 0.055 | 8.301 | 0.145 | 18.710 | 0.141 | 17.828 |

| Day 9 | | Day 11 | | Day 14 | | Day 16 | |
|---|---|---|---|---|---|---|---|
| area | % variat. | area | % variat. | area | % variat. | area | % variat. |
| 0.26 | 66.879 | 0.221 | −71.8471 | 0.107 | −86.3694 | 0.042 | −94.6497 |
| 0.522 | −22.4368 | 0.217 | −67.7563 | 0.057 | −91.5305 | 0 | −100 |
| 0.401 | −48.9172 | 0.374 | −52.3567 | 0.15 | −80.8917 | 0.096 | −87.7707 |

TABLE 3B-continued

Wound healing data - Experiment 3
Phosphate buffer

| | | | | | | | |
|---|---|---|---|---|---|---|---|
| 0.601 | −33.3703 | 0.324 | −64.0798 | 0.103 | −88.5809 | 0.038 | −95.7871 |
| 0.535 | −31.8471 | 0.358 | −54.3949 | 0.15 | −80.8917 | 0.04 | −94.9045 |
| 0.382 | −44.9568 | 0.238 | −65.7061 | 0.128 | −81.5562 | 0.053 | −92.3631 |
| 0.46 | −37.2442 | 0.3 | −59.0723 | 0.1 | −86.3574 | 0.058 | −92.0873 |
| 0.255 | −61.7117 | 0.264 | −60.3604 | 0.101 | −84.8348 | 0.102 | −84.6847 |
| 0.297 | −61.3281 | 0.269 | −64.974 | 0.025 | −96.7448 | 0 | −100 |

Mean ± S.D.

| | | | | | | | |
|---|---|---|---|---|---|---|---|
| 0.413 | −45.410 | 0.285 | −62.283 | 0.102 | −86.418 | 0.048 | −93.583 |
| 47.474 | 15.475 | 0.058 | 6.308 | 0.041 | 5.300 | 0.036 | 5.084 |

| Day 18 | | Day 21 | | Day 23 | |
|---|---|---|---|---|---|
| area | % variat. | area | % variat. | area | % variat. |
| 0 | −100 | 0 | −100 | 0 | −100 |
| 0 | −100 | 0 | −100 | 0 | −100 |
| 0 | −100 | 0 | −100 | 0 | −100 |
| 0.008 | −99.1131 | 0 | −100 | 0 | −100 |
| 0.012 | −98.4713 | 0.012 | −98.4713 | 0 | −100 |
| 0.041 | −94.0922 | 0.008 | −98.8473 | 0 | −100 |
| 0.008 | −98.9086 | 0 | −100 | 0 | −100 |
| 0.092 | −86.1862 | 0.095 | −85.7357 | 0 | −100 |
| 0 | −100 | 0 | −100 | 0 | −100 |

Mean ± S.D.

| | | | | | |
|---|---|---|---|---|---|
| 0.018 | −97.419 | 0.013 | −98.117 | 0.000 | −100.000 |
| 0.031 | 4.611 | 0.031 | 4.680 | 0.000 | 0.000 |

TABLE 3C

Wound healing data - Experiment 3
Component B (004–001) 4 μg

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.826 | 0.604 | −26.8765 | 0.512 | −38.0145 | 0.293 | −64.5278 | 0.248 | −69.9758 |
| 0.731 | 0.635 | −13.1327 | 0.515 | −29.5486 | 0.371 | −49.2476 | 0.324 | −55.6772 |
| 0.785 | 0.659 | −16.051 | 0.538 | −31.465 | 0.43 | −45.2229 | 0.358 | −54.3949 |
| 0.803 | 0.742 | −7.59651 | 0.601 | −25.1557 | 0.49 | −38.9788 | 0.427 | −46.8244 |
| 0.727 | 0.691 | −4.95186 | 0.676 | −7.01513 | 0.509 | −29.9862 | 0.468 | −35.6259 |
| 0.785 | 0.581 | −25.9873 | 0.506 | −35.5414 | 0.379 | −51.7197 | 0.278 | −64.586 |
| 0.866 | 0.523 | −39.6074 | 0.329 | −62.0092 | 0.218 | −74.8268 | 0.161 | −81.4088 |
| 0.757 | 0.666 | −12.0211 | 0.582 | −23.1176 | 0.407 | −46.2351 | 0.319 | −57.86 |
| 0.799 | 0.526 | −34.1677 | 0.319 | −60.0751 | 0.236 | −70.4631 | 0.169 | −78.8486 |
| 0.81 | 0.568 | −29.8765 | 0.430 | −46.9136 | 0.374 | −53.8272 | 0.292 | −63.9506 |

Mean ± S.D.

| | | | | | | | |
|---|---|---|---|---|---|---|---|
| 0.789 | 0.620 | −21.027 | 0.501 | −35.886 | 0.371 | −52.504 | 0.304 | −60.915 |
| 0.043 | 0.072 | 11.842 | 0.114 | 16.883 | 0.098 | 13.987 | 0.099 | 13.999 |

| Day 9 | | Day 11 | | Day 14 | | Day 16 | |
|---|---|---|---|---|---|---|---|
| area | % variat. | area | % variat. | area | % variat. | area | % variat. |
| 0.187 | −77.3608 | 0.106 | −87.1671 | 0.02 | −97.5787 | 0 | −100 |
| 0.208 | −71.5458 | 0.132 | −81.9425 | 0 | −100 | 0 | −100 |
| 0.223 | −71.5924 | 0.102 | −87.0064 | 0 | −100 | 0 | −100 |
| 0.283 | −64.7572 | 0.126 | −84.3088 | 0.01 | −98.7547 | 0 | −100 |
| 0.311 | −57.2215 | 0.145 | −80.055 | 0 | −100 | 0 | −100 |
| 0.188 | −76.051 | 0.008 | −98.9809 | 0 | −100 | 0 | −100 |
| 0.138 | −84.0647 | 0.008 | −99.0762 | 0 | −100 | 0 | −100 |
| 0.264 | −65.1255 | 0.135 | −82.1664 | 0.042 | −94.4518 | 0 | −100 |
| 0.173 | −78.3479 | 0.081 | −89.8623 | 0 | −100 | 0 | −100 |
| 0.212 | −73.8272 | 0.082 | −89.8765 | 0 | −100 | 0 | −100 |

Mean ± S.D.

| | | | | | | | |
|---|---|---|---|---|---|---|---|
| 0.219 | −71.989 | 0.093 | −88.044 | 0.007 | −99.079 | 0.000 | −100.000 |
| 0.053 | 7.837 | 0.049 | 6.662 | 0.014 | 1.817 | 0.000 | 0.000 |

TABLE 3C-continued

Wound healing data - Experiment 3
Component B (004–001) 4 μg

| Day 18 | | Day 21 | | Day 23 | |
|---|---|---|---|---|---|
| area | % variat. | area | % variat. | area | % variat. |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |
| 0 | −100 | 0 | −100 | 0 | −100 |

Mean ± S.D.

| 0 | −100.000 | 0 | −100 | 0 | −100 |
| 0.000 | 0.000 | 0.000 | 0.000 | 0.000 | 0.000 |

TABLE 3D

Wound healing data - Experiment 3
Component B (004-001) 2μg

| Day 0 | Day 1 | | Day 3 | | Day 5 | | Day 7 | | Day 9 | | Day 11 | |
|---|---|---|---|---|---|---|---|---|---|---|---|---|
| area | area | % variat. | area | % variat. | area | % variat. | area | % variat. | area | % variat. | area | % variat. |
| 0.776 | 0.591 | −23.8402 | 0.577 | −25.6443 | 0.285 | −63.6943 | 0.202 | −74.2675 | 0.173 | −77.7062 | 0.063 | −91.8814 |
| 0.785 | 0.548 | −30.1911 | 0.447 | −43.0573 | 0.357 | −53.9948 | 0.309 | −60.1804 | 0.229 | −70.828 | 0.093 | −88.1529 |
| 0.776 | 0.68 | −12.3711 | 0.587 | −24.3557 | 0.435 | −44.0874 | 0.319 | −58.9974 | 0.246 | −68.299 | 0.056 | −92.7835 |
| 0.778 | 0.498 | −35.990 | 0.194 | −75.0643 | 0.179 | −76.933 | 0.112 | −85.567 | 0.107 | −86.2468 | 0 | −100 |
| 0.776 | 0.428 | −44.845 | 0.183 | −76.4175 | 0.152 | −81.071 | 0.092 | −88.543 | 0.008 | −98.9691 | 0 | −100 |
| 0.803 | 0.638 | −20.548 | 0.597 | −25.6538 | 0.427 | −44.183 | 0.365 | −52.2876 | 0.141 | −82.4408 | 0.08 | −90.0374 |
| 0.765 | 0.72 | −5.882 | 0.657 | −14.1176 | 0.496 | −41.3018 | 0.357 | −57.7515 | 0.316 | −58.6928 | 0.181 | −76.3399 |
| 0.845 | 0.591 | −30.059 | 0.512 | −39.4083 | 0.427 | −47.284 | 0.337 | −58.3951 | 0.196 | −76.8047 | 0.086 | −89.8225 |
| 0.81 | 0.669 | −17.407 | 0.567 | −30 | 0.518 | −36.0494 | 0.355 | −56.1728 | 0.28 | −65.4321 | 0.188 | −76.7901 |
| 0.834 | 0.631 | −24.341 | 0.469 | −43.765 | 0.316 | −60.2416 | 0.233 | −70.6844 | 0.153 | −81.1111 | 0.008 | −99.0408 |

Mean ± S.D.

| 0.7948 | 0.599 | −24.547 | 0.479 | −39.748 | 0.359 | −54.884 | 0.268 | −66.285 | 0.185 | −76.653 | 0.076 | −90.485 |
| 0.027 | 0.089 | 11.398 | 0.165 | 21.096 | 0.125 | 15.301 | 0.103 | 12.797 | 0.090 | 11.531 | 0.067 | 8.532 |

| Day 14 | | Day 16 | | Day 18 | | Day 21 | | Day 23 | |
|---|---|---|---|---|---|---|---|---|---|
| area | % variat. | area | % variat. | area | % variat. | area | % variat. | area | % variat. |
| 0 | −100 | 0 | −100 | 0 | −100 | 0 | −100 | 0 | −100 |
| 0 | −100 | 0 | −100 | 0 | −100 | 0 | −100 | 0 | −100 |
| 0.007 | −99.0979 | 0 | −100 | 0 | −100 | 0 | −100 | 0 | −100 |
| 0 | −100 | 0 | −100 | 0 | −100 | 0 | −100 | 0 | −100 |
| 0 | −100 | 0 | −100 | 0 | −100 | 0 | −100 | 0 | −100 |
| 0 | −100 | 0 | −100 | 0 | −100 | 0 | −100 | 0 | −100 |
| 0.114 | −85.098 | 0 | −100 | 0 | −100 | 0 | −100 | 0 | −100 |
| 0 | −100 | 0 | −100 | 0 | −100 | 0 | −100 | 0 | −100 |
| 0.106 | −86.9136 | 0.053 | −93.4568 | 0 | −100 | 0 | −100 | 0 | −100 |
| 0 | −100 | 0 | −100 | 0 | −100 | 0 | −100 | 0 | −100 |

Mean ± S.D.

| 0.023 | −97.111 | 0.005 | −99.346 | 0.000 | −100.000 | 0.000 | −100.000 | 0.000 | −100.000 |
| 0.046 | 5.875 | 0.017 | 2.069 | 0.000 | 0.000 | 0.000 | 0.000 | 0.000 | 0.000 |

TABLE 3E

Wound healing data - Experiment 3
Component B (004-001) 1 mg/kg, i.v.

| Day 0 | Day 1 | | Day 3 | | Day 5 | | Day 7 | | Day 9 | | Day 11 | |
|---|---|---|---|---|---|---|---|---|---|---|---|---|
| area | area | % variat. | area | % variat. | area | % variat. | area | % variat. | area | % variat. | area | % variat. |
| 0.702 | 0.532 | −24.2165 | 0.233 | −66.8091 | 0.159 | −77.3504 | 0.18 | −74.359 | 0.106 | −84.9003 | 0.012 | −98.2906 |
| 0.713 | 0.545 | −23.5624 | 0.401 | −43.7588 | 0.321 | −54.979 | 0.311 | −56.3815 | 0.229 | −67.8822 | 0.088 | −87.6578 |
| 0.854 | 0.731 | −14.4028 | 0.608 | −28.8056 | 0.447 | −47.6581 | 0.43 | −49.6487 | 0.324 | −62.0609 | 0.127 | −85.1288 |
| 0.698 | 0.597 | −14.470 | 0.421 | −39.6848 | 0.321 | −54.0115 | 0.297 | −57.4499 | 0.204 | −70.7736 | 0.027 | −96.1318 |
| 0.702 | 0.591 | −15.812 | 0.459 | −34.6154 | 0.329 | −53.1339 | 0.301 | −57.1225 | 0.137 | −80.4843 | 0.043 | −93.8746 |
| 0.791 | 0.529 | −33.123 | 0.433 | −45.2592 | 0.329 | −58.4071 | 0.263 | −66.7509 | 0.137 | −82.6802 | 0.008 | −98.9886 |
| 0.799 | 0.611 | −23.529 | 0.387 | −51.5645 | 0.231 | −71.0889 | 0.113 | −85.8573 | 0.053 | −93.3667 | 0 | −100 |
| 0.842 | 0.791 | −6.057 | 0.462 | −45.1306 | 0.418 | −50.3563 | 0.352 | −58.1948 | 0.307 | −63.5392 | 0.138 | −83.6105 |
| 0.834 | 0.628 | −24.700 | 0.481 | −42.3261 | 0.393 | −52.8777 | 0.311 | −62.7098 | 0.2 | −76.0192 | 0.072 | −91.3669 |
| 0.886 | 0.818 | −7.675 | 0.694 | −21.6704 | 0.55 | −37.9233 | 0.54 | −39.0519 | 0.39 | −55.9819 | 0.212 | −76.0722 |

Mean ± S.D.

| 0.7821 | 0.637 | −18.755 | 0.458 | −41.962 | 0.350 | −55.779 | 0.310 | −60.753 | 0.209 | −73.769 | 0.073 | −91.112 |
| 0.072 | 0.106 | 8.482 | 0.125 | 12.373 | 0.110 | 11.255 | 0.119 | 12.906 | 0.106 | 11.734 | 0.069 | 7.858 |

| | Day 14 | | Day 16 | | Day 18 | | Day 21 | | Day 23 | |
|---|---|---|---|---|---|---|---|---|---|---|
| | area | % variat. | area | % variat. | area | % variat. | area | % variat. | area | % variat. |
| | 0 | −100 | 0 | −100 | 0 | −100 | 0 | −100 | 0 | −100 |
| | 0 | −100 | 0 | −100 | 0 | −100 | 0 | −100 | 0 | −100 |
| | 0.007 | −99.1803 | 0.008 | −99.0632 | 0 | −100 | 0 | −100 | 0 | −100 |
| | 0 | −100 | 0 | −100 | 0 | −100 | 0 | −100 | 0 | −100 |
| | 0 | −100 | 0 | −100 | 0 | −100 | 0 | −100 | 0 | −100 |
| | 0 | −100 | 0 | −100 | 0 | −100 | 0 | −100 | 0 | −100 |
| | 0 | −100 | 0 | −100 | 0 | −100 | 0 | −100 | 0 | −100 |
| | 0.011 | −98.6936 | 0 | −100 | 0 | −100 | 0 | −100 | 0 | −100 |
| | 0 | −100 | 0 | −100 | 0 | −100 | 0 | −100 | 0 | −100 |
| | 0.013 | −98.5327 | 0 | −100 | 0 | −100 | 0 | −100 | 0 | −100 |

Mean ± S.D.

| | 0.003 | −99.641 | 0.001 | −99.906 | 0.000 | −100.000 | 0.000 | −100.000 | 0.000 | −100.000 |
| | 0.005 | 0.600 | 0.003 | 0.296 | 0.000 | 0.000 | 0.000 | 0.000 | 0.000 | 0.000 |

Table 4A

Wound healing data - Experiment 4
Phosphate buffer

| Day 0 | Day 1 | | Day 3 | | Day 5 | | Day 7 | | Day 9 | | Day 11 | |
|---|---|---|---|---|---|---|---|---|---|---|---|---|
| area | area | % variat. | area | % variat. | area | % variat. | area | % variat. | area | % variat. | area | % variat. |
| 0.813 | 0.817 | 0.492005 | 0.785 | −3.44403 | 0.393 | −51.6605 | 0.297 | −63.4686 | 0.269 | −66.9127 | 0.173 | −78.7208 |
| 0.813 | 0.809 | −0.492 | 0.817 | 0.492005 | 0.462 | −43.1734 | 0.541 | −33.4563 | 0.3 | −63.0996 | 0.19 | −76.6298 |
| 0.954 | 0.981 | 2.830189 | 0.912 | −4.40252 | 0.672 | −29.5597 | 0.584 | −38.7841 | 0.481 | −49.5807 | 0.407 | −57.3375 |
| 0.833 | 0.821 | −1.441 | 0.716 | −14.0456 | 0.48 | −42.377 | 0.404 | −51.5006 | 0.345 | −58.5834 | 0.264 | −68.3073 |
| 0.841 | 0.882 | 4.875 | 0.878 | 4.399524 | 0.758 | −9.8692 | 0.694 | −17.4792 | 0.522 | −37.931 | 0.271 | −67.7765 |
| 0.813 | 0.805 | −0.984 | 0.608 | −25.2153 | 0.407 | −49.9385 | 0.393 | −51.6605 | 0.283 | −65.1907 | 0.289 | −64.4526 |
| 0.805 | 0.821 | 1.988 | 0.746 | −7.32919 | 0.544 | −32.4224 | 0.444 | −44.8447 | 0.361 | −55.1553 | 0.285 | −64.5963 |
| 0.769 | 0.825 | 7.282 | 0.762 | −0.91027 | 0.69 | −10.2731 | 0.657 | −14.5644 | 0.472 | −38.6216 | 0.311 | −59.5579 |
| 0.845 | 0.874 | 3.432 | 0.845 | 0 | 0.639 | −24.3787 | 0.636 | −24.7337 | 0.374 | −55.7396 | 0.352 | −58.3432 |
| 0.817 | 0.829 | 1.469 | 0.789 | −3.42717 | 0.496 | −39.2901 | 0.387 | −52.6316 | 0.246 | −69.8898 | 0.261 | −68.0539 |

Mean ± S.D.

| 0.830 | 0.846 | 1.945 | 0.786 | −5.388 | 0.554 | −33.294 | 0.504 | −39.312 | 0.365 | −56.070 | 0.280 | −66.378 |
| 0.8303 | 0.054 | 2.757 | 0.087 | 8.563 | 0.127 | 14.919 | 0.136 | 16.428 | 0.097 | 11.175 | 0.069 | 7.193 |

| | Day 14 | | Day 16 | | Day 18 | | Day 21 | | Day 23 | |
|---|---|---|---|---|---|---|---|---|---|---|
| | area | % variant. | area | % variat. | area | % variat. | area | % variat. | area | % variat. |
| | 0.125 | −84.6248 | 0.091 | −88.8069 | 0.071 | −91.2669 | 0.009 | −98.893 | 0 | −100 |
| | 0.182 | −77.6138 | 0.062 | −92.3739 | 0.044 | −94.5879 | 0 | −100 | 0 | −100 |
| | 0.365 | −61.74 | 0.227 | −76.2055 | 0.099 | −89.6226 | 0.27 | −71.6981 | 0 | −100 |
| | 0.239 | −71.3085 | 0.112 | −86.5546 | 0.072 | −91.3565 | 0 | −100 | 0 | −100 |

Table 4A-continued

Wound healing data - Experiment 4
Phosphate buffer

|  |  |  |  |  |  |  |  |  |  |
|---|---|---|---|---|---|---|---|---|---|
| 0.173 | −79.4293 | 0.137 | −83.7099 | 0.092 | −89.0606 | 0.031 | −96.3139 | 0 | −100 |
| 0.168 | −79.3358 | 0.124 | −84.7478 | 0.069 | −91.5129 | 0 | −100 | 0 | −100 |
| 0.214 | −73.4161 | 0.074 | −90.8075 | 0.043 | −94.6584 | 0 | −100 | 0 | −100 |
| 0.271 | −64.7594 | 0.155 | −79.844 | 0.031 | −95.9688 | 0.28 | −63.5891 | 0 | −I00 |
| 0.264 | −68.7574 | 0.148 | −82.4852 | 0.047 | −94.4379 | 0 | −100 | 0 | −100 |
| 0.19 | −76.7442 | 0.112 | −86.2913 | 0.066 | −91.9217 | 0.008 | −99.0208 | 0 | −100 |

Mean ± S.D.

|  |  |  |  |  |  |  |  |  |  |
|---|---|---|---|---|---|---|---|---|---|
| 0.219 | −73.773 | 0.124 | −85.183 | 0.063 | −92.439 | 0.060 | −92.951 | 0.000 | −100.000 |
| 0.069 | 7.162 | 0.047 | 4.925 | 0.022 | 2.334 | 0.114 | 13.522 | 0.000 | 0.000 |

TABLE 4B

Wound healing data - Experiment 4
Bovine Serum Albumin

| Day 0 | Day 1 | | Day 3 | | Day 5 | | Day 7 | |
|---|---|---|---|---|---|---|---|---|
| area | area | % variat. | area | % variat. | area | % variat. | area | % variat. |
| 0.785 | 0.821 | 4.585987 | 0.805 | 2.547771 | 0.765 | −2.54777 | 0.622 | −20.7643 |
| 0.857 | 0.858 | 0.116686 | 0.786 | −8.28471 | 0.65 | −24.154 | 0.625 | −27.0712 |
| 0.837 | 0.874 | 4.42055 | 0.825 | −1.43369 | 0.746 | −10.8722 | 0.544 | −35.006 |
| 0.781 | 0.817 | 4.609475 | 0.794 | 1.664533 | 0.708 | −9.34699 | 0.611 | −21.767 |
| 0.853 | 0.924 | 8.323564 | 0.882 | 3.399766 | 0.735 | −13.8335 | 0.668 | −21.6882 |
| 0.845 | 0.895 | 5.91716 | 0.785 | −7.10059 | 0.727 | −13.9645 | 0.618 | −26.8639 |
| 0.833 | 0.893 | 7.202881 | 0.878 | 5.402161 | 0.675 | −18.9676 | 0.453 | −45.6182 |
| 0.854 | 0.916 | 7.259953 | 0.899 | 5.269321 | 0.712 | −16.6276 | 0.48 | −43.7939 |

Mean ± S.D.

| | | | | | | | | |
|---|---|---|---|---|---|---|---|---|
| 0.831 | 0.875 | 5.305 | 0.832 | 0.183 | 0.715 | −13.789 | 0.578 | −30.322 |
| 0.031 | 0.040 | 2.553 | 0.047 | 5.327 | 0.038 | 6.513 | 0.077 | 9.993 |

| Day 9 | | Day 11 | | Day 14 | | Day 16 | |
|---|---|---|---|---|---|---|---|
| area | % variat. | area | % variat. | area | % variat. | area | % variat. |
| 0.538 | −31.465 | 0.344 | −56.1783 | 0.244 | −68.9172 | 0.169 | −78.4713 |
| 0.557 | −35.0058 | 0.368 | −57.0595 | 0.329 | −61.6103 | 0.162 | −81.0968 |
| 0.413 | −50.6571 | 0.287 | −65.7109 | 0.226 | −72.9988 | 0.101 | −87.9331 |
| 0.554 | −29.0653 | 0.329 | −57.8745 | 0.259 | −66.8374 | 0.138 | −82.3303 |
| 0.448 | −47.4795 | 0.352 | −58.7339 | 0.239 | −71.9812 | 0.173 | −79.7186 |
| 0.561 | −33.6095 | 0.299 | −64.6154 | 0.255 | −69.8225 | 0.21 | −75.1479 |
| 0.314 | −62.3049 | 0.255 | −69.3878 | 0.22 | −73.5894 | 0.166 | −80.072 |
| 0.404 | −52.6932 | 0.266 | −68.8525 | 0.239 | −72.0141 | 0.166 | −80.5621 |

Mean ± S.D.

| | | | | | | | |
|---|---|---|---|---|---|---|---|
| 0.474 | −42.785 | 0.313 | −62.302 | 0.251 | −69.721 | 0.161 | −80.667 |
| 0.092 | 12.097 | 0.042 | 5.443 | 0.034 | 3.979 | 0.031 | 3.631 |

| Day 18 | | Day 21 | | Day 23 | | Day 25 | |
|---|---|---|---|---|---|---|---|
| area | % variat. | area | % variat. | area | % variat. | area | % variat. |
| 0.062 | −92.1019 | 0.007 | −99.1083 | 0 | −100 | 0 | −100 |
| 0.039 | −95.4492 | 0.021 | −97.5496 | 0 | −100 | 0 | −100 |
| 0 | −100 | 0.000 | −100 | 0 | −100 | 0 | −100 |
| 0.081 | −89.6287 | 0.031 | −96.0307 | 0 | −100 | 0 | −100 |
| 0.094 | −88.9801 | 0.055 | −93.5522 | 0.018 | −97.8898 | 0 | −100 |
| 0.145 | −82.8402 | 0 | −100 | 0 | −100 | 0 | −100 |
| 0.083 | −90.036 | 0.008 | −99.0396 | 0 | −100 | 0 | −100 |
| 0.107 | −87.4707 | 0 | −100 | 0 | −I00 | 0 | −100 |

Mean ± S.D.

| | | | | | | | |
|---|---|---|---|---|---|---|---|
| 0.076 | −90.813 | 0.015 | −98.160 | 0.002 | −99.736 | 0.000 | −100.000 |
| 0.044 | 5.178 | 0.020 | 2.329 | 0.006 | 0.746 | 0.000 | 0.000 |

We claim:

1. Method of treatment of wounds, ulcers and other traumatic lesions to any of the tissues in the body, comprising administering an effective amount of Component B, together with a pharmaceutically acceptable carrier.

* * * * *